(12) United States Patent
Walter et al.

(10) Patent No.: US 8,790,278 B2
(45) Date of Patent: Jul. 29, 2014

(54) ORTHOPAEDIC SAFETY SYSTEM

(75) Inventors: William Lindsay Walter, Waverton (AU); Ronald Mark Gillies, Enmore (AU); Shane McCarthy Donohoo, Castle Hill (AU)

(73) Assignee: Silesco Pty Ltd, Waverton, NSW (AU)

( * ) Notice: Subject to any disclaimer, the term of this patent is extended or adjusted under 35 U.S.C. 154(b) by 817 days.

(21) Appl. No.: 12/920,016

(22) PCT Filed: Feb. 26, 2009

(86) PCT No.: PCT/AU2009/000219
§ 371 (c)(1),
(2), (4) Date: Mar. 15, 2011

(87) PCT Pub. No.: WO2009/105817
PCT Pub. Date: Sep. 3, 2009

(65) Prior Publication Data
US 2011/0264009 A1    Oct. 27, 2011

(30) Foreign Application Priority Data

Feb. 29, 2008 (AU) .............................. 2008901009
Mar. 4, 2008 (AU) .............................. 2008901066
Jun. 5, 2008 (AU) .............................. 2008902854

(51) Int. Cl.
*A61B 5/00* (2006.01)
(52) U.S. Cl.
USPC ........................................................ 600/587

(58) Field of Classification Search
USPC ......... 600/553, 587; 73/379.04, 862, 862.392
See application file for complete search history.

(56) References Cited

U.S. PATENT DOCUMENTS

| | | | |
|---|---|---|---|
| 5,494,045 A * | 2/1996 | Kiviranta et al. ............. 600/587 |
| 5,657,763 A * | 8/1997 | Schneider ..................... 600/553 |
| 5,766,137 A * | 6/1998 | Omata .......................... 600/587 |
| 5,938,182 A * | 8/1999 | Goodrich et al. ............. 254/209 |
| 6,034,296 A | 3/2000 | Elvin et al. |
| 7,879,043 B2 * | 2/2011 | Meneghini et al. ............. 606/99 |
| 8,246,553 B2 * | 8/2012 | Sakagami et al. ............. 600/587 |
| 2003/0069644 A1 | 4/2003 | Kovacevic et al. |
| 2006/0032314 A1 | 2/2006 | Hnat et al. |
| 2006/0189898 A1 | 8/2006 | Nitzan et al. |
| 2007/0233267 A1 | 10/2007 | Amirouche et al. |

OTHER PUBLICATIONS

International Search Report for Application No. PCT/AU2009/000219, dated May 11, 2009, 5 pages.
International Preliminary Report on Patentability for Application No. PCT/AU2009/000219, dated Sep. 10, 2010, 8 pages.

* cited by examiner

*Primary Examiner* — Max Hindenburg
(74) *Attorney, Agent, or Firm* — Sterne, Kessler, Goldstein & Fox P.L.L.C.

(57) ABSTRACT

An orthopaedic device for generating one or more strain signals representative of the strain in a bone in response to a force applied to the bone. The device includes an encircling member (11) for encircling the bone of a subject and a sensor member (13) connected thereto, the sensor member including a strain sensor (14). In a preferred embodiment the strain sensor comprises one or more bridging members configured to break when subjected to a particular strain.

13 Claims, 19 Drawing Sheets

ORTHOPAEDIC SAFETY SYSTEM

CROSS-REFERENCE TO RELATED APPLICATIONS

The present application claims priority from Australian Provisional Patent Application No 2008901009 filed on 29 Feb. 2008, Australian Provisional Patent Application No 2008901066 filed on 4 Mar. 2008, Australian Provisional Patent Application No 2008902854 filed on 5 Jun. 2008, the contents of which are incorporated herein by reference.

FIELD OF THE INVENTION

The present invention relates to a device for monitoring the strain in a bone to enable a user to evaluate the risk of fracture during or after an orthopaedic procedure.

BACKGROUND ART

Orthopaedic implants are typically mechanically hammered into position either through use of a mallet or a repetitive automated hammer. In both cases, force is applied by a mallet/hammer and through an impactor to an implant. Bone preparation typically uses a broach which may be hammered into the bone—the force being applied through a broach handle. On some occasions a trial implant may be hammered into the bone—the force being applied through an impactor or handle.

While a certain force is required to drive the implant into position, the force must not be so high that it causes fracturing of the bone.

Particularly, one complication associated with the implant process is the formation of a longitudinal split in the bone known as a periprosthetic fracture (PPF) which results from hoop stress in the bone (created by insertion of the implant or broach or trial implant) exceeding the strength of bone. PPFs are a significant cause of intraoperative morbidity and one of the most common causes of early post-operative failure of prosthetic components.

PPF is a particularly serious complication of Total Hip Arthroplasty (THA) and occur around both acetabular and the femoral components. The incidence of PPF is significantly higher in revision procedures than it is in primary procedures. The incidence of PPF is also significantly higher in cementless or press fit procedures than in cemented procedures. The incidence is also higher in the elderly and in those with fragile bone.

PPF can be divided into three time-based categories; Intra-operative fractures detected at the time of surgery, fractures in the early post operative period, and postoperative fractures occurring late after procedure.

The incidence of PPFs detected at the time of surgery have been reported in primary cementless femoral implantations to be as high as 5.4%. In revision femora, the incidence of femoral fracture detected at the time of surgery is much higher with cementless revision procedures being reported as high as 21%. The prevalence of these fractures has increased since the introduction of cementless press fit acetabular components. However, there still is surprisingly little in the orthopaedic literature regarding acetabular PPF at the time of surgery.

Further, the problem of intra-operative PPF in both the femur and acetabulum might be more prevalent than reported. It is argued that fractures occurring in the early post operative period may well be undiagnosed intra-operative PPFs. Whatever the incidence of intra-operative PPF the severity of the problem is highlighted by the poor outcomes reported.

Currently, there is no useful mechanism by which a surgeon can determine the risk of fracture both during and after an operative procedure.

The present invention aims to address the abovementioned shortcomings and provide a safety system to minimise the risk of fracture during and after implant procedures.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In a first aspect, the present invention provides an orthopaedic device comprising:

an encircling member configured to encircle a bone of a subject; and a sensor member connected to said encircling member, said sensor member including a strain sensor;

wherein said strain sensor generates one or more strain signals representative of the strain in said bone in response to a force applied to said bone.

In a second aspect, the present invention provides a method for monitoring the strain in a bone during or following an orthopaedic procedure, said method including:

encircling an encircling member around a bone of a subject wherein said encircling member is connected to or comprises a sensor member, said sensor member including a strain sensor which generates one or more signals representative of the strain in said bone in response to a force applied to said bone during or following the orthopaedic procedure.

In a third aspect, the present invention provides an orthopaedic device comprising:

an encircling member configured to at least partially encircle a bone of a subject; and a sensor member connected to said encircling member, said sensor member including a strain sensor;

wherein said strain sensor generates one or more strain signals representative of the strain in said bone in response to a force applied to said bone.

The sensor member may further include, or be connected to, processing means to process the one or more strain signals. The processing means may provide at least one output signal.

Still further, the sensor member may comprise or be connected to an output means to present said at least one output signal. The output means may comprise at least one indicia means. Said indicia means may include a visual indicator including a light or a series of lights which reflect the level of strain in said bone. The lights of the indicia means may be graded to depict a visual spectrum from relatively low strain in the bone to severe strain and risk of fracture.

Other visual indicators of the level of strain are envisaged. For example, the output signals may be plotted on a spectral plot.

The output means may present said at least one output signal as one or more auditory signals representative of said spectrum of strain in the bone. For example, the auditory signals may increase in frequency and/or strength reflecting a change in strain from a relatively low strain through to severe strain and risk of fracture.

In a preferred embodiment, the sensor member includes a threshold detector. Once a threshold strain in the bone is reached, the sensor member may generate an alarm signal. The alarm signal may be an auditory signal. Alternatively, the alarm signal may be a visual signal, for example a flashing light.

The sensor member may measure deformation of the bone caused by force applied to said bone. The force may be applied by a number of orthopaedic devices. Still further, the force on the bone may be imparted by a prosthetic component during implantation or affixation of said prosthetic component to or in said bone. In one embodiment, the prosthetic component is a femoral component of a total or partial hip prosthesis wherein said femoral component comprises a shaft and a spherical head. The shaft is implanted into the femur from the proximal end of the femur such that the head is positioned to co-operate with an acetabular component. While the femur is presented as one example, the present invention may be used in any orthopaedic procedure and on any bone of a subject wherein a force is imparted upon said bone during or after said procedure and wherein said device of the invention monitors the strain in said bone and enables a user to determine the risk of fracture of the bone.

Implantation of the shaft into the femur can exert significant force on the femur such that the bone is under strain. If the strain exceeds a threshold level then a fracture results. The force required to insert the femoral component often results in a large radial force which causes a radial deformation or strain in the bone.

The deformation of a bone may be measured by said strain sensor. The strain sensor may comprise a mechanical sensor, an optical sensor, an acoustical sensor, a pneumatic sensor, or an electrical sensor.

The strain sensor may comprise an electrical sensor. In this embodiment, the electrical sensor may include a series of wires or a foil arranged in a grid pattern. The wires are typically mounted on a backing member. The wires and/or foil may be made from any one or more of the following materials including Constantan (copper-nickel alloy), Nichrome V (nickel-chrome alloy), platinum alloys (for example tungsten), Isoelastic (nickel-iron alloy), or Karma-type alloy wires (nickel-chrome alloy), or semiconductor materials including germanium and silicon.

The electrical strain sensor typically forms part of the encircling member which when in situ encircles the bone of a subject. Any strain on the bone will be transferred to the encircling member and thus to the strain sensor.

When the bone of a subject is subjected to a force which results in strain in the bone, the deformation of the bone is transferred to the electrical strain sensor such that the wires or foil may also be deformed. Such deformation causes a change in electrical resistance in said wires/foil. Accordingly, in this embodiment, the change in electrical resistance in the wires or foil comprises said at least one strain signal.

As noted above, the sensor member may further comprise a processing means. Typically, the processing means comprises a strain transducer. The strain transducer may comprise an electrical circuit. Typically the electrical circuit comprises four strain gauge elements electrically connected to form a Wheatstone bridge. In this embodiment, the transducer measures the resistance (strain signals) and converts said signals to said one or more output signal. In this embodiment, said one or more output signals are expressed as millivolts out per volt of excitation voltage (mV/V).

When measuring the strain in a bone during a procedure, the one or more output signals are typically relatively low-level voltage signals. This may render the sensor member particularly susceptible to noise from other electrical devices, thus increasing the error rate of the sensor member. Accordingly, the sensor member may further include a shielding member to shield said noise.

Still further, the sensor member may comprise an amplifier. The processed signal of the strain member is relatively small and typically less than 10 mV/V (10 mV of output per volt of excitation voltage). The amplifier typically amplifies the signal level to increase measurement resolution and improve signal-to-noise ratios.

Further, the sensor member may include a filtering means. The filtering means may remove high-frequency noise from other electrical equipment.

The backing member of the strain sensor is typically made of a dielectric material. Examples of suitable material include paper, epoxies, acrylics, epoxy polyimide, polyimide, polyester, and stainless steel alloys. In one embodiment, the backing member is made from polyimide.

The strain sensor may also include a protective coating. Examples of suitable coating material include silicone rubber, microcrystalline wax, chloroprene rubber, epoxy resins, butyl rubber The strain sensor may further comprise a series of bridging members wherein said bridging members are configured such that they are compromised when subjected to a particular strain level. In one embodiment, the bridging members may each include frangible regions. A first bridging member may break upon being subjected to a first strain; a second bridging member may break when subjected to a second and increased level of strain and so on. The degree of strain required to break each bridging member may differ and may be calibrated such that upon breakage of a certain bridging member, a signal would generate to a user that the strain was at a level to increase the risk of fracture. The "signal" in this embodiment may simply comprise a visual indicator wherein a user has a direct view of the bridging members. In another embodiment, the bridging members may be connected to an electrical transducer to convert the mechanical change to an electrical signal indicative of the strain in the bone.

Further, each bridging member may comprise an electrical conductor. Breaking of a bridging member may increase the resistance across the circuit formed by the members. Each bridging member may also vary in thickness and/or material such that the increase in resistance upon breaking of one bridging member may differ from the increases in resistance due to the breaking of another member.

The encircling member may comprise a compression member which encircles a bone and applies a compressive force to counterbalance an outward radial force exerted by a prosthetic component. In one embodiment, the encircling member may comprise an elongate band. The elongate band may extend from a first end to a second end. Further, the encircling member may include at least one locking member to fasten the encircling member around a bone. The locking member may comprise a number of structures to hold the band in place around the bone such that any displacement of the bone causes a displacement of the band.

The elongate band typically has an upper surface and a lower, bone engaging surface wherein said upper surface comprises a series of teeth. The locking member comprises a receiving member positioned at one end of the elongate band.

When the elongate band is disposed around a bone, the receiving member receives the other end of the elongate band and such that the other end may be moved through said receiving member. The receiving member includes at least one pawl member configured to engage the teeth of the elongate band. The individual teeth may comprise a sloped face or ramp to allow the pawl member to ride over said teeth. Typically, however, the opposite face of each tooth is substantially perpendicular to the elongate band such that it forms a block. In this configuration, a "toothed" portion of the elongate band may be moved through the receiving member in a forward direction but is prevented from moving in the opposite direction by way of abutment of the pawl member with said blocking face of the teeth.

In a further embodiment, the locking member may comprise a swage type fastener wherein the receiving member may comprise a tubular or other type of hollow member. Said receiving member may be compressed to lock the elongate band received therein.

The locking member may also comprise a separate clamping member configured to clamp the elongate band around the bone in a tensioned state.

The encircling member further includes or is connected to a tensioning member which increases or decreases the tension in the elongate band when it encircles the bone.

The encircling member may be made from a metallic stainless steel alloy, titanium alloy or a cobalt chrome alloy material. Alternatively, the encircling member may be made from a monofilament or woven polymeric material such as nylon, and polypropylene. In one embodiment, the encircling member may be made from a woven fabric material.

The strain sensor may be disposed in or on the elongate band. Alternatively, the strain sensor may be disposed in or on the tensioning member. In particular the strain sensor may be disposed on the tensioning member to sense the change in length of the tensioning member. In this embodiment, the strain sensor may be attached to the tensioning member by gluing or welding. Further, in this embodiment, the strain sensor may receive signals via insulated leads incorporated into the tensioning member.

In an embodiment of the third aspect of the invention, the encircling member may, not fully encircle the bone in use but rather comprise a resiliently flexible member which may be clipped onto the bone.

In a further aspect, the safety system of the present invention provides a system for implanting an orthopaedic implant, said system comprising:
 an implant;
 at least one driving member configured to transfer a force to the implant; and
 at least one force limiting member configured to allow the transfer of a driving force to drive the implant into a bone but prevent the transfer of a force above a pre-determined range to said implant; wherein said pre-determined range is less than a force range in which the bone will fracture.

In a further aspect of the safety system, the present invention provides a driving member for an orthopaedic implant system wherein said driving member is configured to transfer a force to an implant to drive the implant into said bone;
 wherein the driving member comprises, or is connected to, a force limiting member configured to allow the transfer of a driving force to drive the implant into a bone but prevent the transfer of a force above a pre-determined range to said implant; wherein said pre-determined range is less than a force range in which the bone will fracture.

The safety system of the preset invention May also provide an orthopaedic implant, said orthopaedic implant comprising or connected to a force limiting member wherein said force limiting member is configured to allow the transfer of a driving force to drive the implant into a bone but prevent the transfer of force above a pre-determined range to said implant; wherein said pre-determined range is less than a force range in which the bone will fracture.

In a further aspect, the present invention provides a force limiting member for an orthopaedic implant system, said force limiting member being configured to allow the transfer of a driving force from a driving member of an orthopaedic implant system to drive the implant into a bone but prevent the transfer of force above a pre-determined range to said implant; wherein said pre-determined range is less than a force range in which the bone will fracture.

In another aspect, the present invention comprises a driving member for an orthopaedic implant system wherein said driving member is configured to transfer a force to an implant to drive the implant into a bone;
 wherein the driving member comprises, or is connected to, a force indicator member which indicates a fracture risk force range to a user.

The safety system may further provide a force indicator member for use with an orthopaedic implant system, said force indicator member comprising a main body having a connection member to connect said main body to a driving member or to an implant of said orthopaedic implant system and wherein said force indicator indicates a fracture risk force range to a user.

In a further aspect, the present invention is a method of implanting an orthopaedic implant into a bone without fracturing said bone, said method including:
 exposing an area of subject bone;
 preparing the bone for insertion of an implant; and
 applying force using a driving member to said implant to drive the implant into the bone; wherein said implant or the driving member comprise or are connected to a force limiting member, wherein said force limiting member prevents the transfer of force above a pre-determined range to said implant; wherein said pre-determined force range is less than a force range at which the bone will fracture.

In another aspect, the present invention is a method of implanting an orthopaedic implant into a bone without fracturing said bone, said method including:
 exposing an area of subject bone;
 preparing the bone for insertion of an implant; and
 applying force using a driving member to said implant to drive the implant into the bone; wherein said implant or the driving member comprise or are connected to a force indicator member, wherein said force indicator member indicates a fracture risk force range to a user.

In a further aspect, the present invention is a system for implanting an orthopaedic implant, said system comprising:
 an implant;
 at least one driving member configured to transfer a force to the implant;
 at least one force limiting member configured to allow the transfer of a driving force to drive the implant into bone but prevent the transfer of a force above a pre-determined range to said implant; wherein said pre-determined range is less than a force range in which a bone will fracture; and
 at least one force indicator member which generates at least one signal representative of a fracture risk force range.

Typically, the force limiting member of the present invention inhibits the transfer of a force of above approximately 1700 to 2000N to a bone of a subject.

The force indicator member typically indicates a force in the range of between 1500 to 2000N, this being the fracture risk range.

The force indictor member may indicate the fracture risk force by a number of means. In one embodiment, the force indicator member comprises a main body having a frangible region. The frangible region may comprise a number of structures with the common feature being that said region breaks when the force indicator member is subjected to a pre-determined force, said pre-determined force being less than the force range required to fracture the bone. The frangible region preferably does not break when the force transferred to the indicator member is within a range suitable for driving the implant into the bone.

In one embodiment, the frangible region comprises a balloon member. Typically, the balloon member is positioned between endplates of the main body such that a force applied to one end of the main body compresses one endplate in a direction towards the other endplate thus sandwiching the balloon therebetween.

The balloon may fail at a particular pressure which may be pre-determined and calculated to reflect the load limit of the bone.

The balloon is typically made from a material selected from any one of the following materials including rubber and silicone.

The balloon may contain therein a marker to enable a user to identify that the balloon has failed and thus the load limit of the bone reached. The marker may include any suitable non-toxic dye.

The marker may be encased within an inner chamber. Said chamber may be made of a transparent material to allow the marker to be viewed.

The force indicator member may also comprise at least one connection member to connect said force indicator member to a driving member or an implant. The connection member may be positioned at one or both ends of the force indicator member. The connection member may comprise an elongate thread extending outwardly from one or both of the endplates. In this embodiment, the force indicator member may be screw threaded onto a driving member or an implant.

The force indicator member may further comprise one or more compression members which deform when subjected to a pre-determined force range. Particularly, said compression member may move from an expanded configuration to a collapsed configuration when subjected to said pre-determined force range. Where more than one compression member is used, they may be configured in series to provide a graded warning system to a surgeon. In this embodiment, a first compression member may deform upon being subjected to a first force range, a second compression member may range and so on.

The driving member of the system typically comprises an impactor member. The impactor member comprises an elongate body extending from a first end to a second end. The first end may comprise a head member having a substantially flat surface for engagement with the head of a mallet or like member. The elongate body may taper towards the second end. Preferably the elongate body tapers in a frustoconical manner and the second end may comprise a substantially flat surface to engage a proximal end of an implant during implantation of said implant.

While the force indicator member may be connected to the driving member such as by screw threaded engagement, the force indicator member may also form part of the driving member and/or the implant. The above description of the embodiments of the force indicator member, therefore, relates to both a separate structure and to a one piece driving member/indicator member and/or implant/indictor member.

The force limiting member of the present invention may comprise a main body extending from a first end to a second end. The main body may comprise connection member at one or both ends to connect the main body to a driving member and/or an implant of an orthopaedic implant system. Alternatively the load limiting member may be integral with the driving member and/or the implant.

In one embodiment, the main body comprises first and a second endplates separated by at least one pivot member. The pivot member typically enables said two endplates to move relative to one another between a relatively spaced state and a relatively compressed state. The endplates may comprise a body having a generally flat upper surface and an opposite lower surface. The upper and lower surfaces are spaced by sidewalls. The plate members are typically oriented such that the lower surface of the first endplate faces the upper surface of the second endplate. The pivot members may extend from the first endplate to the second endplate.

Typically, the force limiting member of this embodiment comprises at least four pivot members with two pivot members extending longitudinally between the sidewalls of the endplates and the other two pivot members extending longitudinally between opposite sidewalls. Each pair of pivot members may be connected by a fuse member. The fuse member may extend transversely from one end located on a pivot member of a pair to a second end located on the other pivot member of the pair. The first end of said fuse member may be connected to the first end of a second fuse member connecting the other pair of oppositely disposed pivot members by a pivot arm. Likewise the second ends of the fuse member may be so connected by a pivot arm.

The fuse member may break when the force limiting member is subjected to a force in said pre-determined range. Alternatively, the fuse member may deform when subjected to said pre-determined force range. In either embodiment, the breaking or the deformation of the fuse member prevents the further transfer of force to the implant.

In a further embodiment, the endplates of the main body may be separated by at least one buckling member. Said one or more buckling member may buckle when the force limiting device is subjected to the pre-determined force. Such buckling of the buckling member(s) may limit the forces transmitted by said force limiting member to the implant such that the further transfer of force is prevented.

The force limiting member may further comprise a spring and damper assembly. The assembly may include one or more valve members which open in the damper to limit the maximum force which can be applied.

The driving member may comprise both an indicator member and a force limiting member. In this embodiment, the force indicator member may indicate a force in a first predetermined range and the force limiting member may prevent the transfer of a force in a second and greater range than said first pre-determined range.

The implant of the present invention may further comprise a force limiting member and/or a force indicator member as described above.

In a further embodiment, the implant may comprise a recessed region at a proximal end to receive the second end of the impactor. The recessed region is defined by sidewalls and a base. The base may comprise a plate member which is configured to fail when subjected to the pre-determined force. Typically, the implant has a void region located beneath said plate member such that when the impactor breaks the plate member, there is no surface upon which it may engage and transfer the force to the implant.

A further aspect of the present safety system provides a device for monitoring fracture risk during implantation of a prosthetic component into a bone, said device comprising;

a tracking system which provides output signals representative of a relative displacement of said prosthetic component in a bone;

a signal processor which receives said output signals and comparatively processes said output signals against reference values to provide an indicator of bone fracture risk.

In another aspect of the safety system there is provided a method for assessing fracture risk during implantation of a prosthetic component into a bone, said method including:

tracking the displacement or acceleration of said prosthetic component during implantation;

obtaining an output signal representative of said displacement;

comparatively processing said output signal against reference values; and providing an indication of bone fracture risk.

The tracking system may comprise an instrument tracker and a bone imaging tracker.

The instrument tracker may comprise a camera unit. The bone imaging tracker may comprises the same or a different camera unit.

The tracking system may also include bone reference markers for digitization of the bone position.

In one embodiment the tracking system comprises a hip navigation system to localize the path of a femoral component as it is inserted into a femur.

The hip navigation system may utilise a software based system for processing the output of the camera unit. The output of the instrument tracker may be comparatively processed by the software against the digitized bone position at regular time intervals.

In one embodiment the digitized bone position is overlayed against Cartesian co-ordinates.

The prosthetic component may be impacted by a mallet to drive the component into the desired position within the bone. The normal pattern is that for each mallet impact the prosthetic component descends into the bone. The magnitude of this displacement decreases with each impact until the component stops descending. An acceleration of the implant will likely indicate a femoral fracture.

In a further embodiment, the impactor or mallet has an accelerometer to measure acceleration rather than displacement.

DETAILED DESCRIPTION OF AN EXEMPLARY EMBODIMENT OF THE INVENTION

Figure 1:
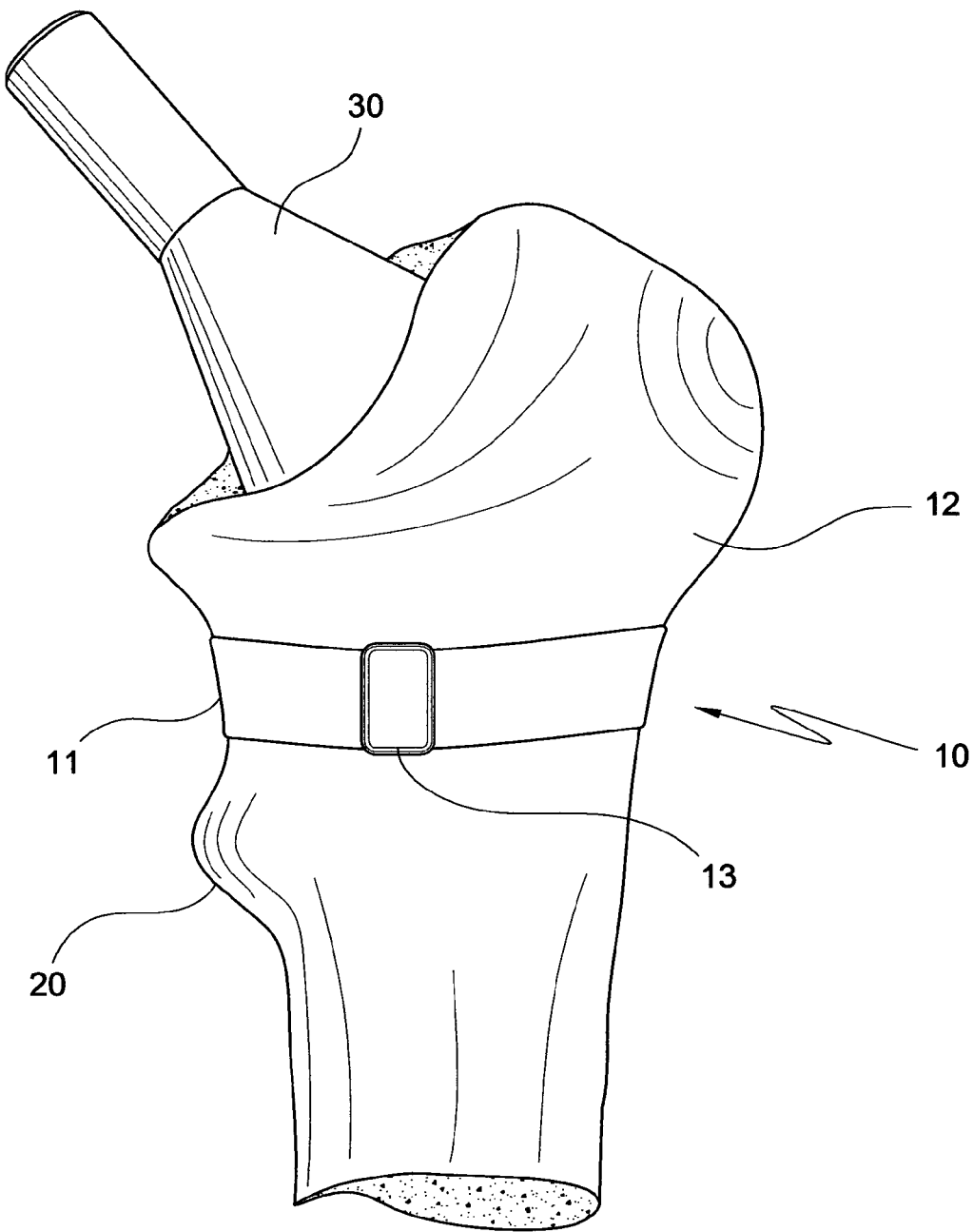
FIG. 1 is a schematic representation of a device with strain sensor according to one aspect of the invention.

The accompanying drawings and associated description relate to a number of aspect of the present invention being a safety system to avoid fracture of a bone during an implant procedure. The safety system may involve the monitoring of strain in the subject bone to avoid placing too great a strain during a procedure. The system also includes devices and methods to limit the force applied to an implant while still enabling sufficient force to seat said implant properly within a bone. Still, further, the safety system as described and depicted herein includes a tracking system to monitor fracture risk during an implant procedure.

In FIGS. 1 to 6 there is provided depiction of a device of a safety system, said device adapted to monitor the strain in a receiving bone.

Strain is the amount of deformation of a body due to an applied force. More specifically, strain is defined as the fractional change in length of said body. Bone strain caused by surgical implantation of prosthetic components may result in periprosthetic fracture.

To enable a user to effectively evaluate the risk of fracture, device 10 measures the strain in a bone and provides data to a user indicative of the risk of fracture to the bone. This aspect of the invention has developed following the finding that, although loads applied to a bone may vary significantly, the strain to fracture ratio is relatively constant. Based on in vitro analysis, device 10 may be calibrated to reflect a spectrum from a safe region of strain through to a danger region of strain ie the risk of fracture is high.

The device 10 has an encircling member 11 which is tensioned around the subject bone 12. The encircling member 11 provides a compressive hoop force on the bone to counterbalance a radially outward force imparted on a bone during an orthopaedic procedure and particularly implantation of a prosthesis in or to the bone. The encircling member 11 itself does have the effect of at least partially increasing the hoop stiffness of the bone and thus may to some extent reduce the risk of fracture to the bone 12.

However, even with an encircling member in place around the bone, the forces involved in implanting a prosthesis are significant and without proper feedback, a surgeon has no way of evaluating the strain in the bone.

The sensor member 13 of the present invention comprises a strain sensor 14 which generates strain signals 15 representative of the strain in the bone 9 in response to the force applied to the bone 12.

Figure 5:
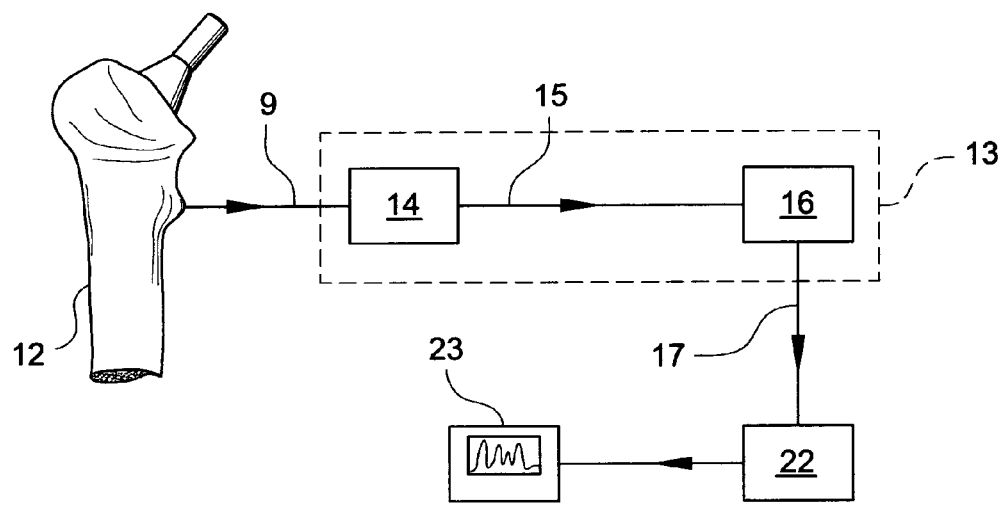
FIG. 5 is a diagram depicting a system using a strain monitoring device.

In addition, and as depicted in FIG. 5, the sensor member may further include processing means 16 to process the strain signals 15. The processing means 16 provides one or more output signals 17 which can be presented in a variety of ways to alert the surgeon to the risk of fracture. Equally, the signals provide a guide in relation to a safe strain zone.

FIG. 1 shows the encircling member 11 tensioned above the lower trochanter 20 of a femur of a subject. Sensor member 13 is disposed on the encircling member 11.

Figure 2:
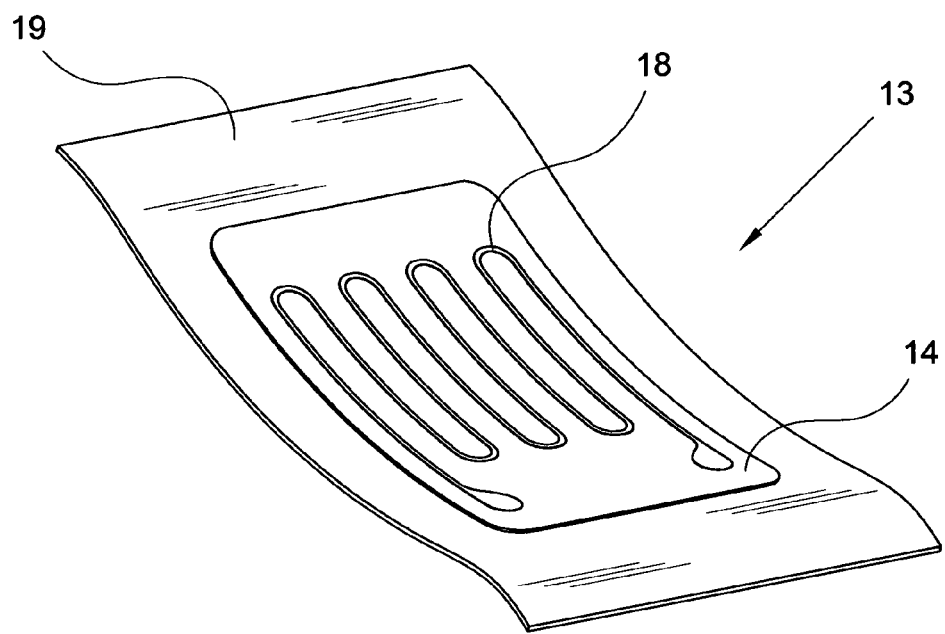
FIG. 2 is a representation of a type of sensor member used with the device depicted in FIG. 1.

Sensor member 13 comprises an electrical strain sensor 14 as depicted in FIG. 2. The electrical strain sensor 14 includes wire 18 arranged in a pattern and mounted on backing member 19. Strain (deformation) in the bone is transferred to the electrical strain sensor 14, via the encircling member 11, which in response also deforms. This deformation causes a change in electrical resistance across the wire 18.

The strain sensor is a resistor which forms part of a Wheatstone bridge. The Wheatstone bridge measures the resistance and converts to an electrical output signal. The Wheatstone bridge is generally classed as a processing means herein and although it would be formed integrally with the sensor 14, for ease of reference, it has been depicted as a separate processing unit 16 in FIG. 5. The device of the present invention may further include a central processing unit (CPU) 22 or other processing means to modify the electrical signal.

The sensor member 13 may also include or be connected to a display unit 23. The display unit 23 provides a visual or auditory indicator relating to the strain in the bone.

Figure 3:
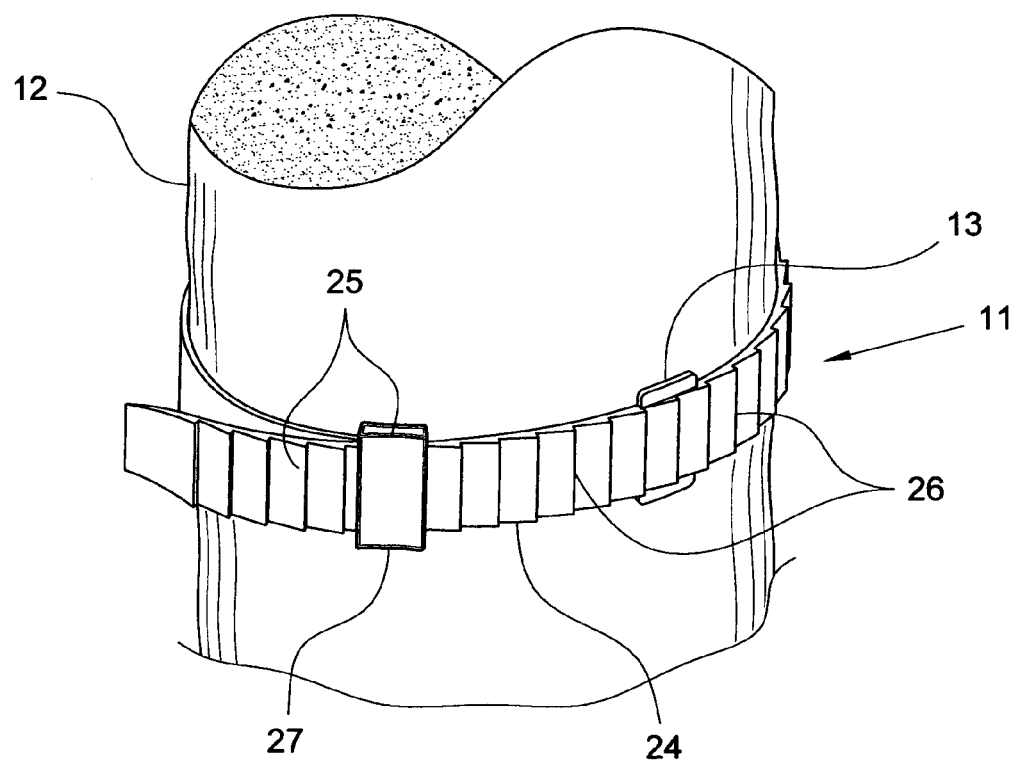
FIG. 3 is a schematic representation of a further embodiment of the device with strain sensor.
Figure 4:
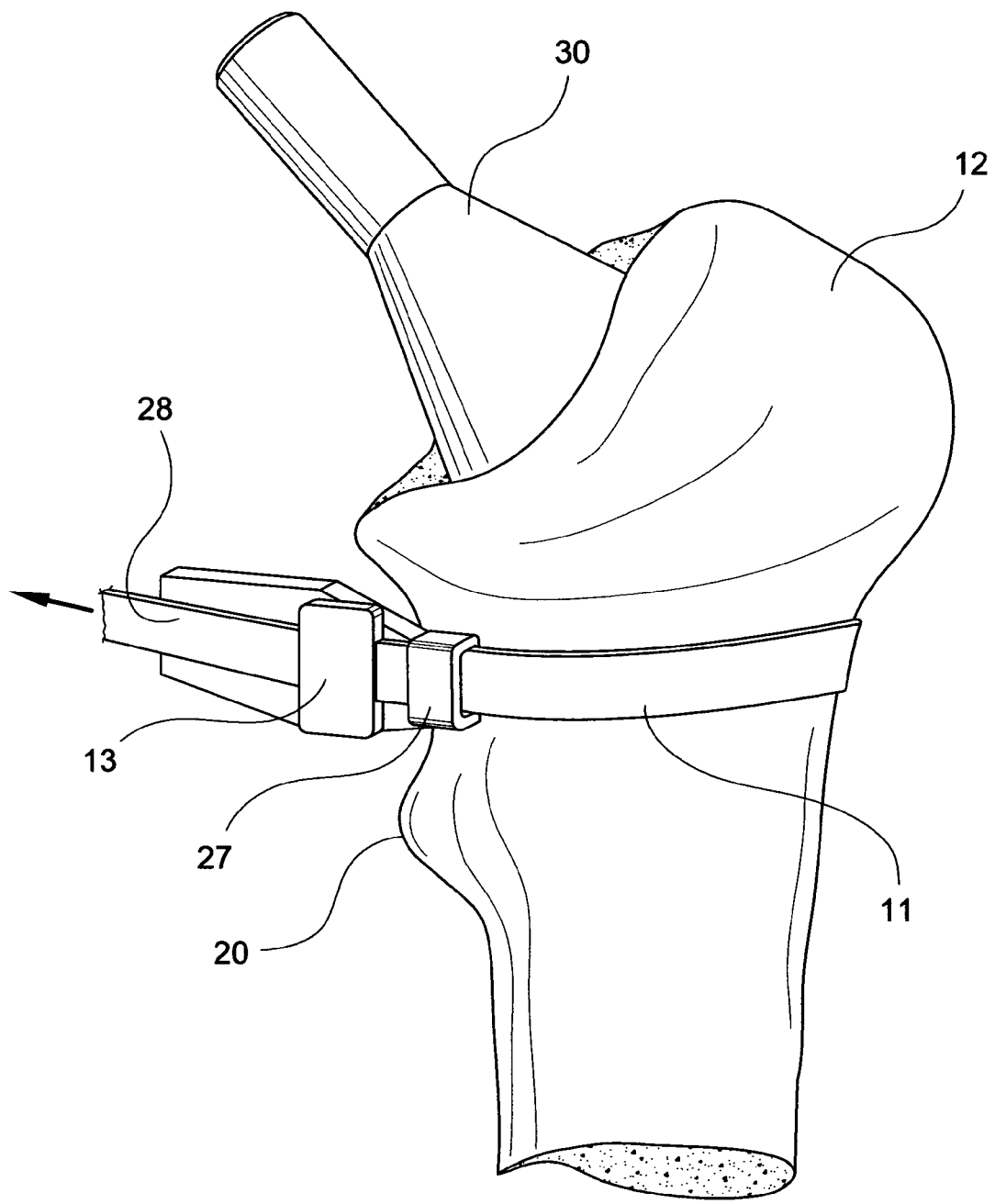
FIG. 4 depicts a still further embodiment a strain monitoring device for use in a safety system.

As depicted in FIGS. 1, 3 and 4 the encircling member 11 is essentially an elongate band 24 which extends from a first end to a second end. The encircling member includes a locking member 25 to fasten the encircling member around a bone.

An upper surface of the elongate band 24 has a series of teeth 26. The locking member comprises a receiving member 27 positioned at one end of the elongate band. When the elongate band is disposed around a bone, the receiving member 27 receives the other end of the elongate band and such that the other end may be moved through the receiving member. The receiving member comprises pawl member (nor depicted) which engages the teeth 26.

As depicted in FIG. 4, the sensor forms part of a tensioning member 28 and senses the change in length of the tensioning member 28.

As an illustrative embodiment, the device may be used during implantation of a femoral component 30 of a hip prosthesis. Prior to implantation, a surgeon wraps the encircling member 11 around a region of the femur adjacent the proximal end of the femur and locks the encircling member by way of locking member 27 in a tensioned state around the bone.

The sensor is connected to any output or processing means required. Upon insertion of the femoral component 30 into the femur, a force is generated which causes the bone to deform. Deformation of the bone causes the wires of the sensor to also deform thus changing the resistance across wire 18. The change in resistance is measured by an electrical transducer which can either output said signal to a display unit 23 or forward the signal to a further processing unit such as a CPU 22 for further processing before forwarding to said display unit 23.

The output signals may be presented in a number of ways from visual to auditory signals as described above.

The constant monitoring of the strain in the bone during the procedure allows a surgeon to control the force applied and thus reduce the risk of periprosthetic fracture. The additional element of providing an alarm signal should a threshold strain be reached provides a safety feature in the prevention of fracture.

Figure 6:
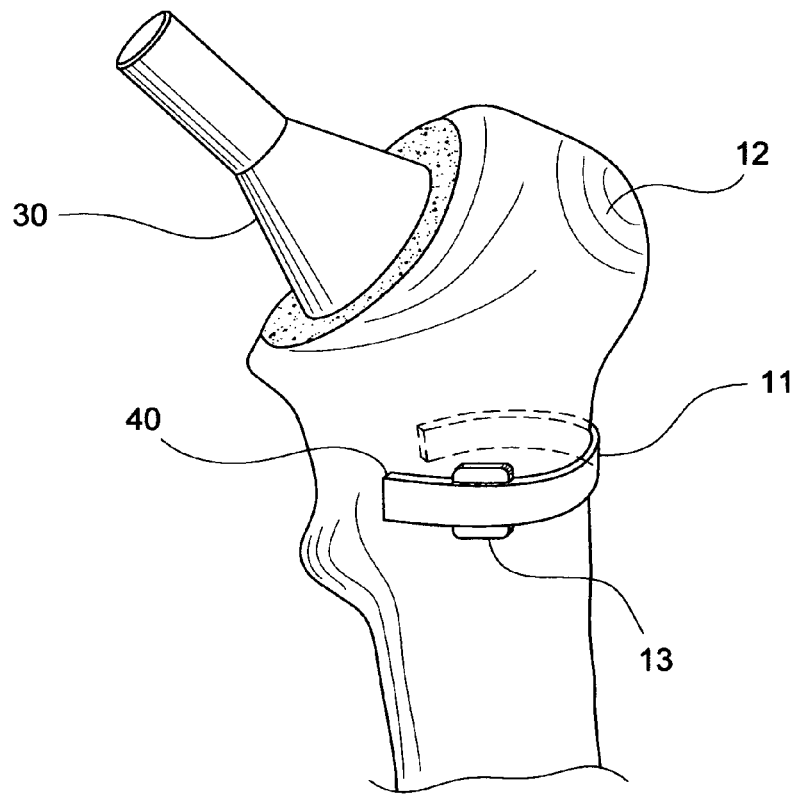
FIG. 6 is a schematic representation of different form of strain monitoring device according to a further aspect of the invention.

A further aspect of the invention is depicted in FIG. 6. The encircling member 40 of this aspect only partially encircles the bone. The encircling member 40 is clipped onto the bone and thus is typically made from a resiliently flexible material.

A further aspect of the safety system is described below and relates to monitoring the force applied to an implant and providing a warning system to enable a surgeon to assess the risk of fracture to a bone.

To effectively implant a prosthetic component in a bone, it is necessary to provide a sufficient driving force to force the prosthetic component ("implant") into said bone. The amount of force required to drive the implant into position increases as the degree of penetration increases.

A certain force is required to ensure a proper "seating" of the implant in the bone and a another force is required to result in fracture of the bone. As the degree of penetration increases and thus the force to cause penetration increases, the risk of applying a force of such magnitude to cause fracture thus increases.

Figure 7:
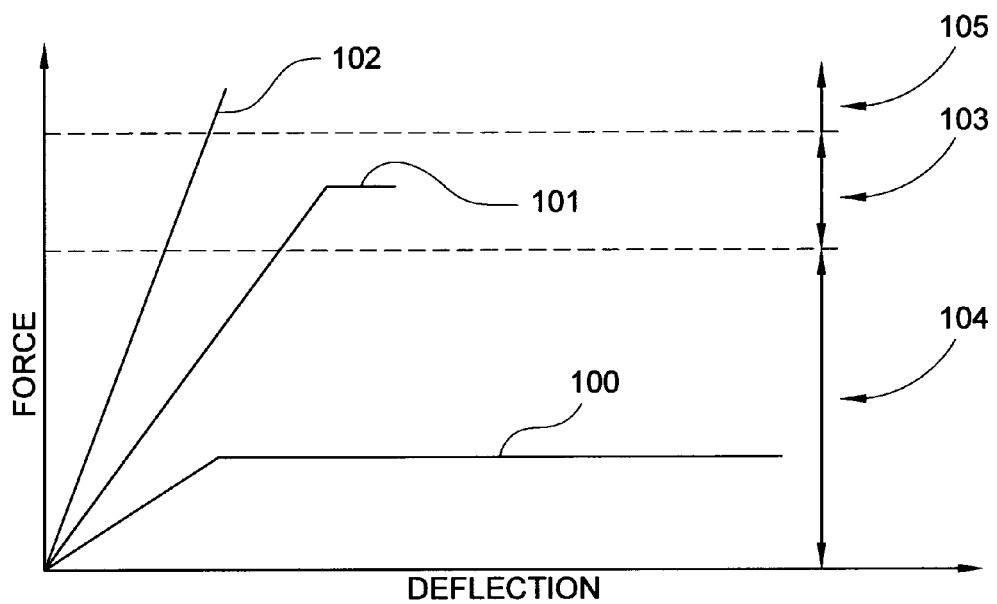
FIG. 7 is a graph showing force and deflection of implants in a bone at various stages of implantation.

FIG. 7 graphically depicts force versus deflection of an implant in a bone. Item 100 represents the forces which are involved in early driving of the implant into the bone. Item 101 relates to a force required to properly seat the implant in the bone. Such force is typically required towards the final stages of penetration. Item 102 depicts a force which will result in fracture.

As the surgeon reaches the final stages of implantation of the implant he/she is aware that a greater force is required to achieve a final penetration to properly seat an implant. The force applied should fall within the zone depicted as 103 in FIG. 7. A force below this as shown as 104 is insufficient to properly seat the implant and a force above as represented by 105 is too high and will likely cause fracture.

Figure 8:
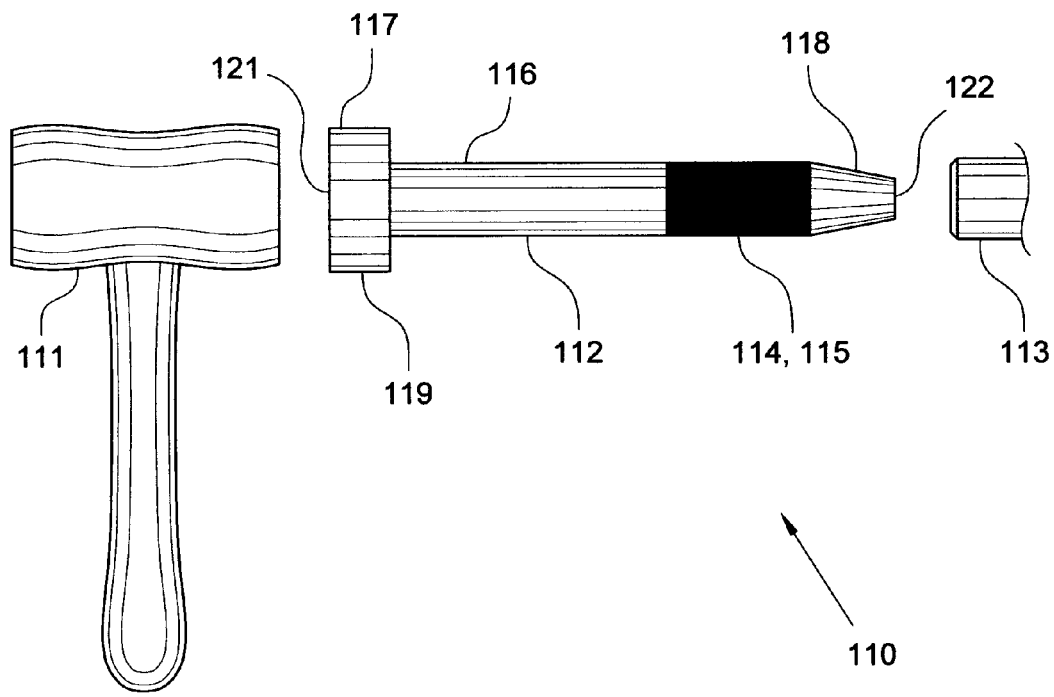
FIG. 8 is a schematic representation of orthopaedic components for use as part of a implant safety system.

Components of an orthopaedic implant system 110 are shown in FIG. 8—mallet 111, impactor 112 and the proximal portion of an implant 113.

The load limiting member 114 or force indicator member 115 of this aspect of the invention may be incorporated in any one of the mallet 111, impactor 112 and implant 113. In FIG. 8, the impactor is depicted as having a load limiting member 114 or force indicator member 115

Impactor 112 is an elongate body 116 which extends from a first end to 117 to a second end 118. The first end 117 is a head member 119 having a substantially flat surface 121 for engagement with the head mallet 111. The impactor tapers towards second end 118 and terminates in a end 122 which engages implant 113 dining implantation.

Figure 9:
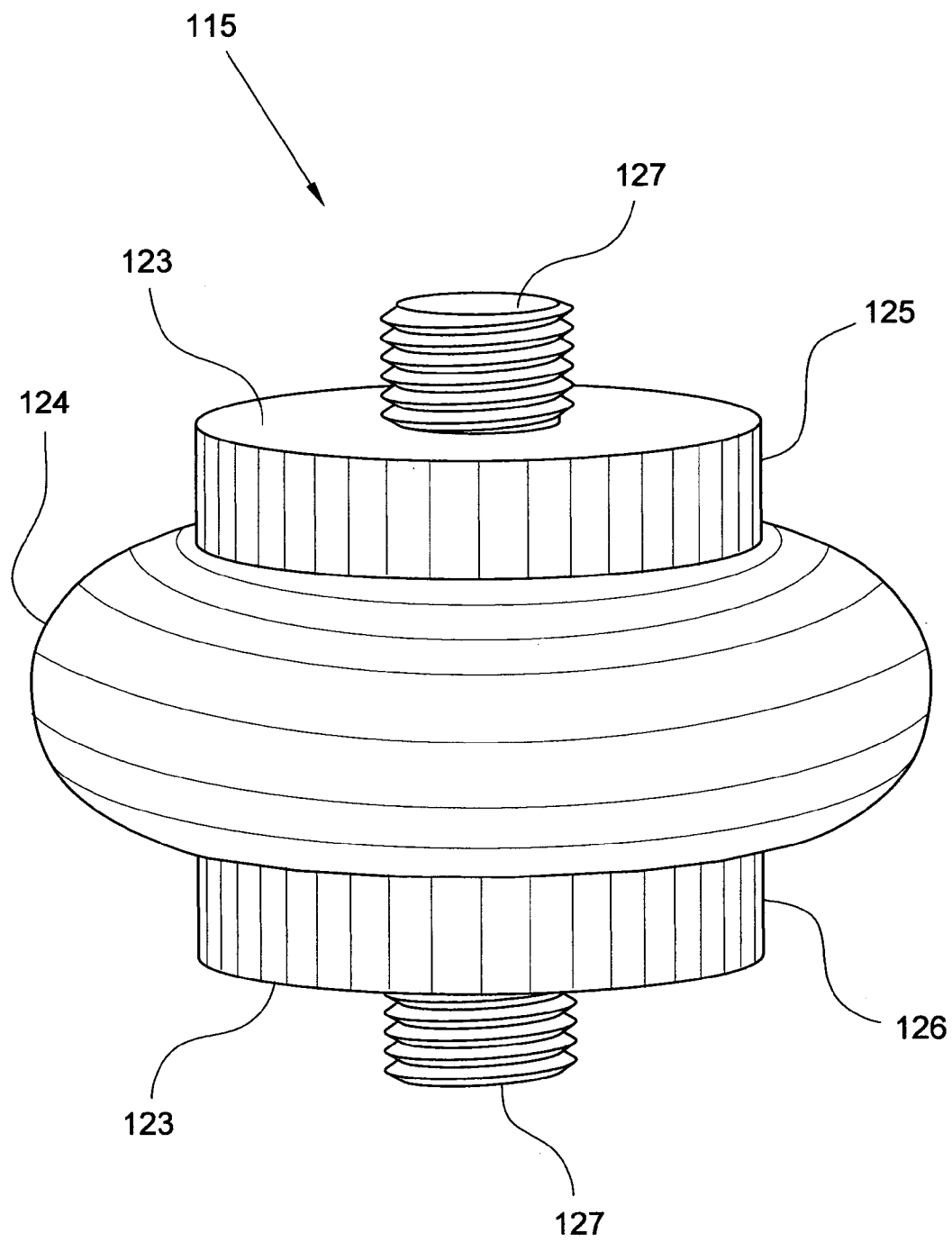
FIGS. 9 to 12 depict an embodiment of a force indicator device.
Figure 10:
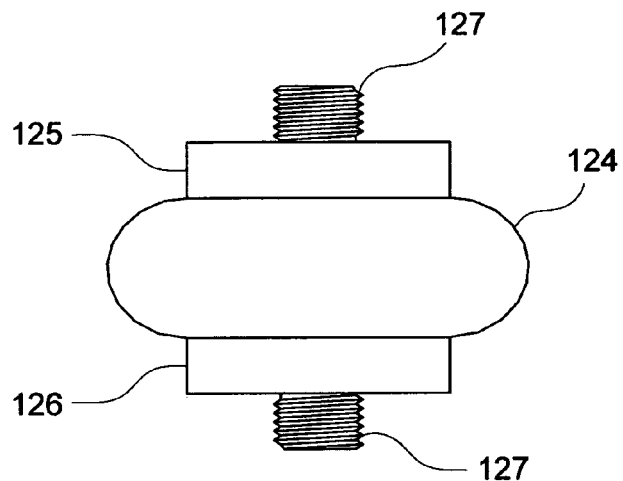
Figure 11:
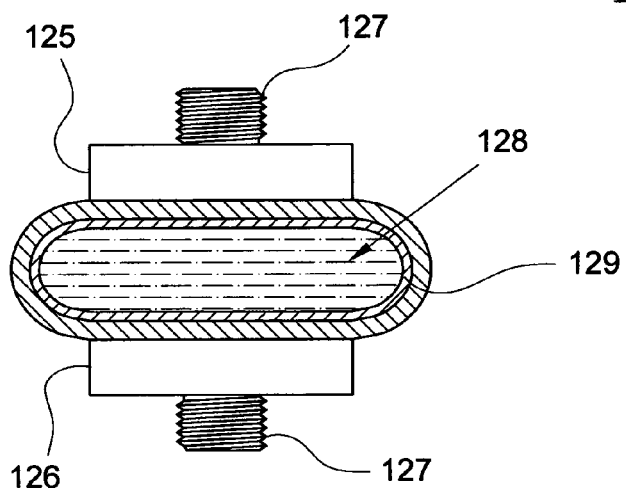

One embodiment of a force indicator member 115 is shown in FIGS. 9 to 11. The indicator member 115 comprises a main body 123 which houses a balloon member 124. The balloon member 124 is sandwiched between first and second endplates 125,126. The force indicator member has a threaded connection member 127 at both ends although it is noted that the thread need only be at one end to enable connection to an impactor, mallet or implant as appropriate.

The balloon member 124 fails at a pre-determined pressure. Balloon member 124 houses a marker such as a dye which becomes visible upon failure of the balloon member. The dye is housed within a transparent chamber 129 to prevent contamination.

Figure 12:
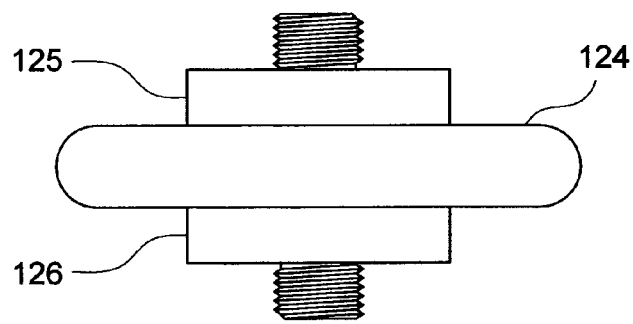

FIG. 12 depicts the force indicator member when subjected to a pre-determined force which reflects an increased likelihood of fracture. Balloon member 124 is compressed between endplates 125 and 126 until it ruptures. The failure or rupture pressure is representative of the load limit of the bone.

Figure 13:
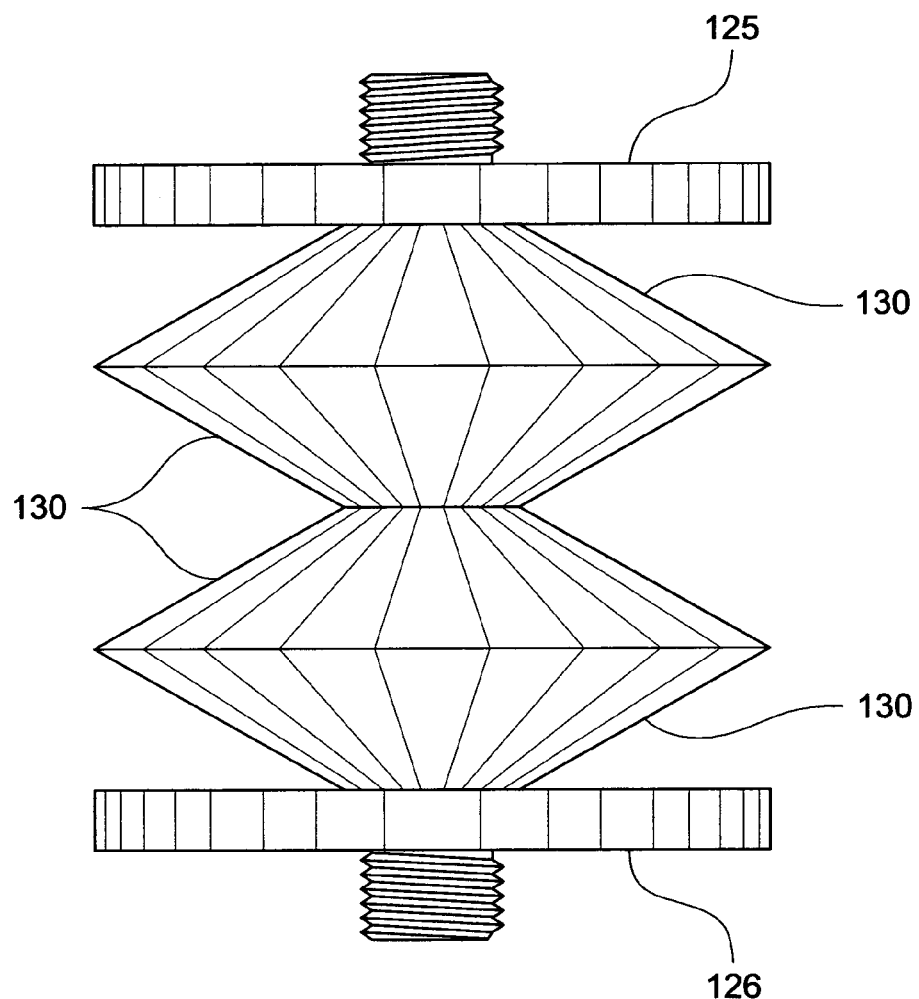
FIGS. 13 to 16 depict a further embodiment of a force indicator device.
Figure 14:
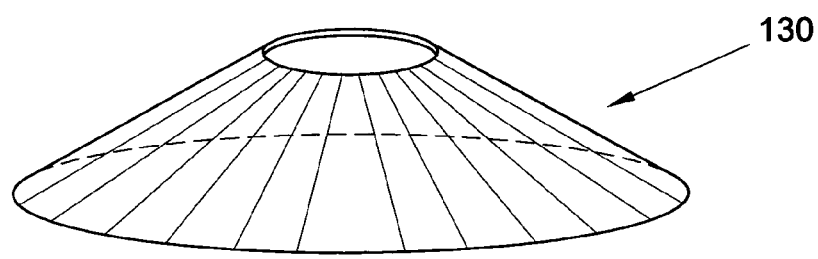

Another embodiment of a force indicator member 115 is depicted in FIGS. 13 to 16. The force indicator member comprises cone washer members 29. The material and geometry of the individual washer will determine the force required to flatten the washer. An example of the structure of an individual washer is shown in FIG. 14.

Figure 15:
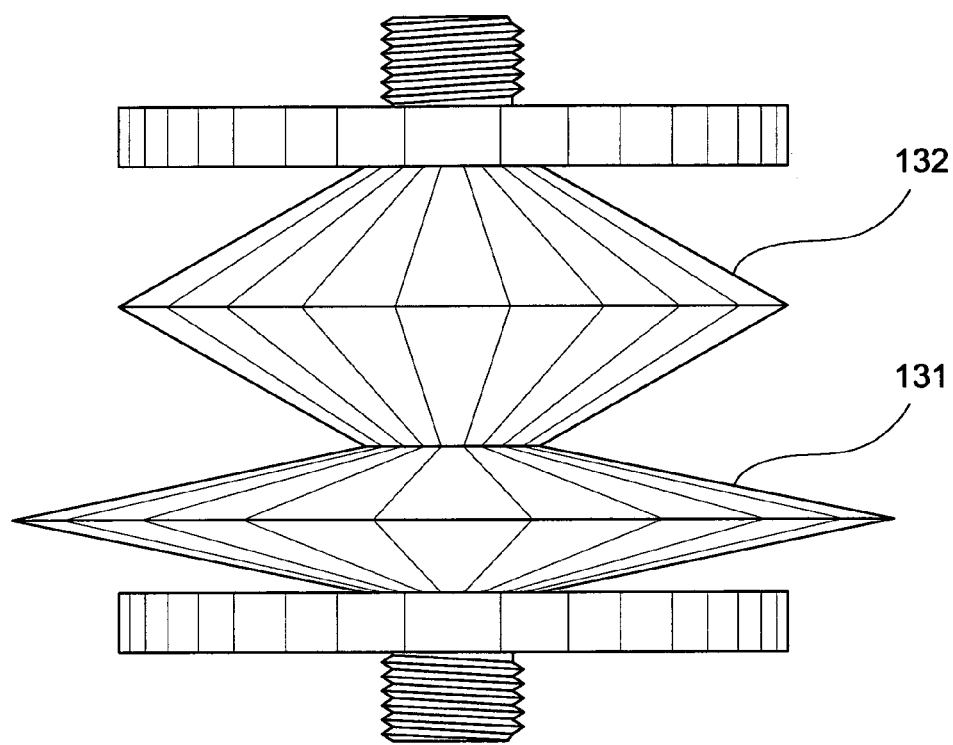
Figure 16:
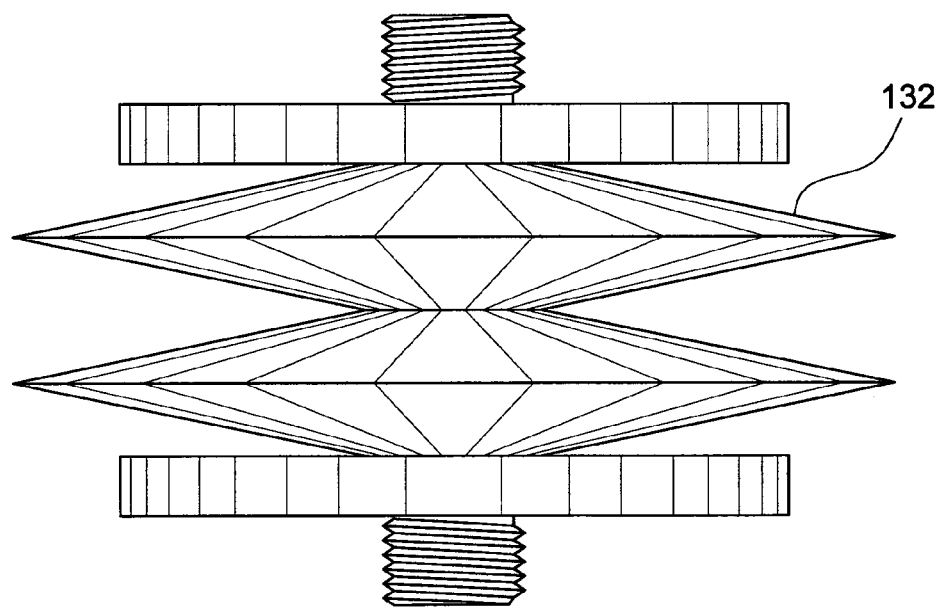

When used in series, the cone washers provide a graded warning system for a surgeon. In FIG. 13, there is not sufficient force to flatten the washers. In FIG. 15, the force indicator member has been subjected to a force sufficient to cause a first washer or a first pair of the washers 131 to collapse. Said washer or pair of washers 131 is configured in either its material and/or shape to deform when subjected to a certain load. In use this load may reflect the seating force for properly seating the implant. A second washer or pair of washers 132 is configured to flatten at a higher load level which reflects a force which has an increased likelihood of causing fracture. If the second washers flatten, as depicted in FIG. 16, a surgeon is thus provided with a second warning and fracture may be imminent if he/she continues.

In addition to or in place of the force indicator member discussed above, an orthopaedic implant system may utilise a force limiting member. In this regard, the safety system involves controlling the amount of force exerted on an implant by a surgeon during an implant procedure.

Figure 17A:
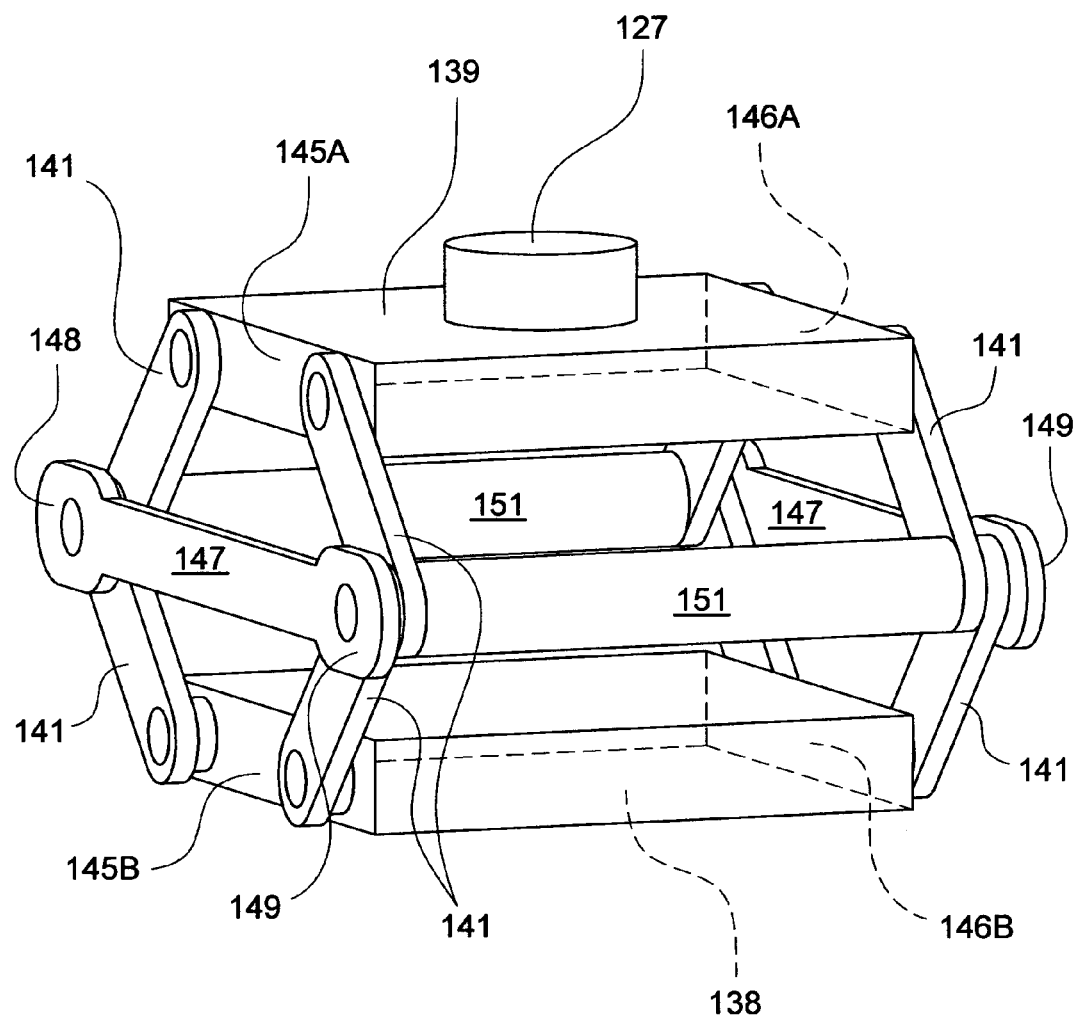
FIGS. 17a to 17c depict an embodiment of a force limiting device.
Figure 17B:
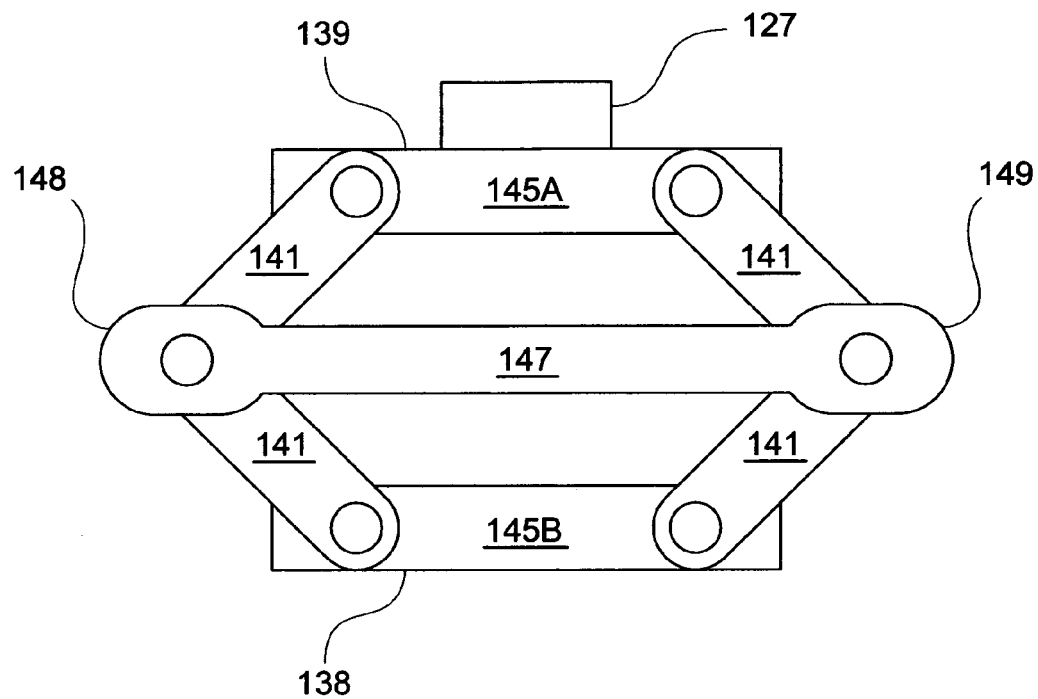
Figure 17C:
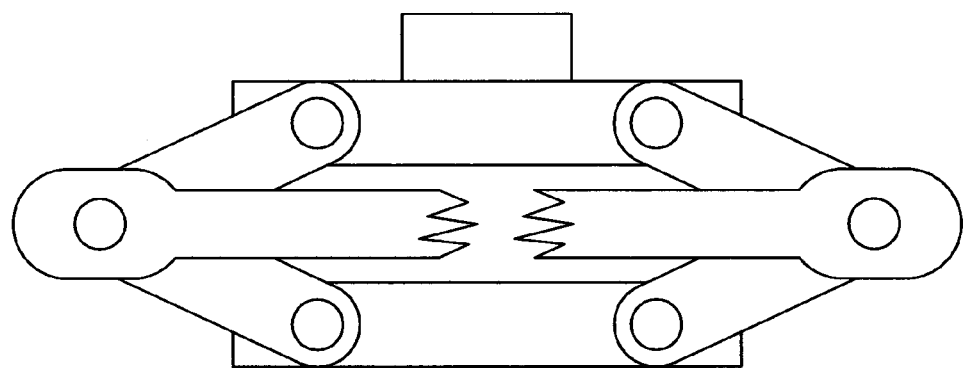

In the embodiments depicted in FIGS. 17a, 17b and 17c, the force limiting member comprises endplates 138 and 139. A connection member 127 extends from one or both of endplates 138 and 139 and connect the force limiting member to an impactor 112 and/or an implant 113.

Endplates 138 and 139 are separated by pivot members 141. The pivot members 141 enable the two endplates to move relative to one another between a spaced state seen in FIG. 17a and the relatively compressed state seen in FIG. 17c.

The embodiment depicted has four pivot members 141 with two pivot members extending longitudinally between the sidewalls 145a and 145b of the endplates and the other two pivot members extending longitudinally between opposite sidewalls 146a and 146b. Each pair of pivot members is connected by fuse member 147. The fuse member 147 extends transversely from one end 148 located mid-way on a pivot member to a second end 149 located midway on its opposite pair pivot member. The fuse members 147 are connected by pivot cross pin 151.

FIG. 17a is a depiction of a scenario where there is insufficient force applied to the force limiting member to cause it to move from its spaced configuration to a compressed configuration. Therefore, the relatively rigid structure shown in this figure will transfer force to an implant.

FIG. 17c depicts the force limiting member of FIG. 17a after it has been subjected to a force which reflects the load limit of the bone. As evident, the compression of the endplates relative to one another causes the pivot members to bow outwardly, tensioning the fuse member until it fails.

Figure 18:
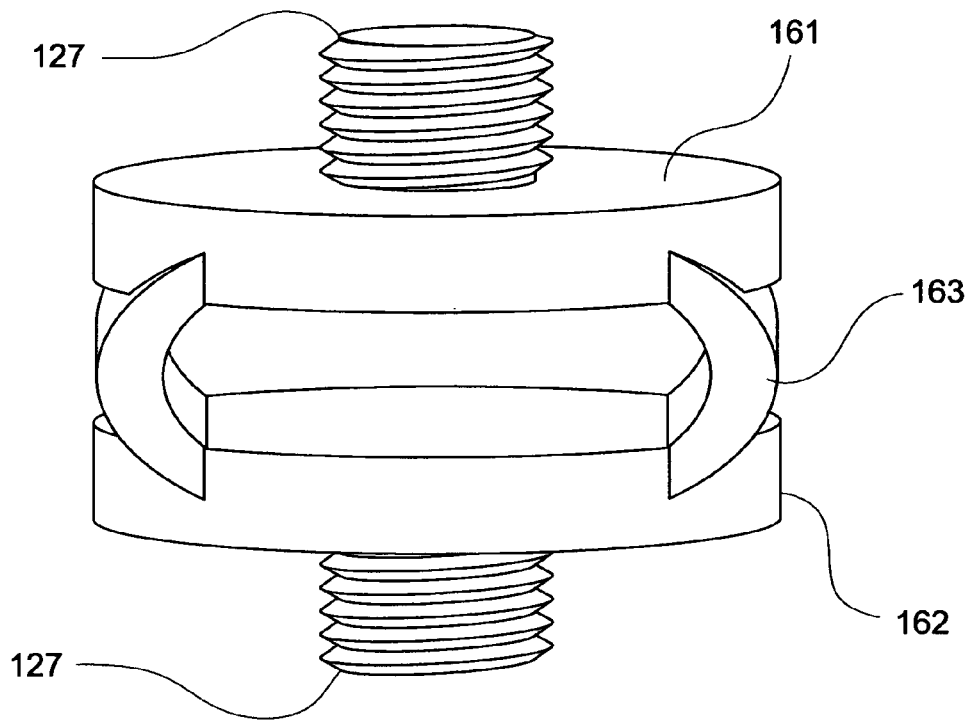
FIG. 18 is a representation of a further force limiting device.

In a further embodiment depicted in FIG. 18, endplates 161 and 162 may be separated by at least one buckling member 163. Said one or more buckling member may buckle when the force limiting device is subjected a force reflecting the load limit of the bone.

Figure 19:
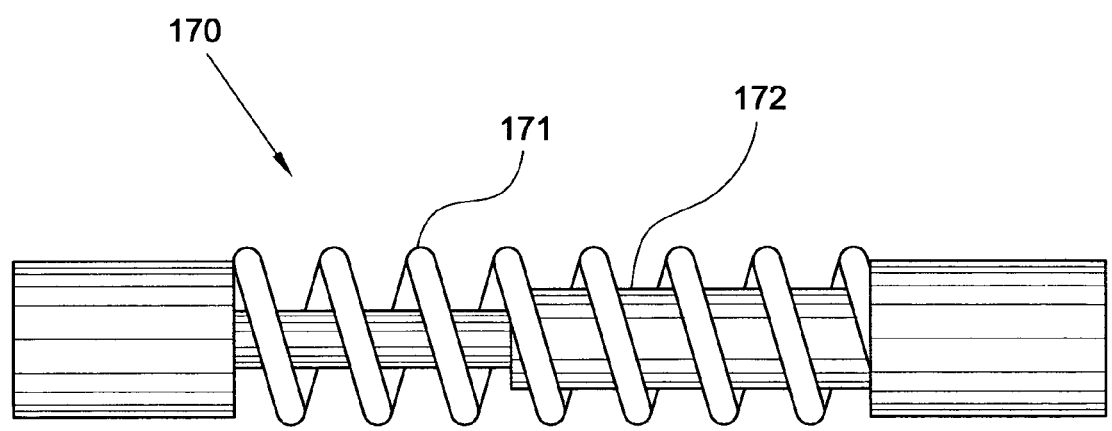
FIG. 19 is a schematic representation of another embodiment of a force limiting device.

The force limiting member may further comprise a spring and damper assembly 170 as shown in FIG. 19. The assembly 170 has a spring 171 and damper 172.

Once a force reaches a certain level, the damper valves open in the damper and limit the force which can be applied to an implant. The limit on the force that may be transferred to the implant reduces the risk of fracture of the bone, particularly at the end stages of seating the implant.

The damper valves are adjustable to adjust the opening when subjected to force. Depending upon the patient and other variables, it may be necessary to have the valves open in response to a greater or a lesser force. In this regard, the force limiting member of this embodiment may comprise a setting member on an exterior surface wherein the setting member enables a user to adjust the setting between a range, say 1 to 5 with setting 1 suitable for older/lighter patients with an increased likelihood of fracture and level 5 suitable for heavier/younger patients with a reduced chance of fracture.

Figure 21:
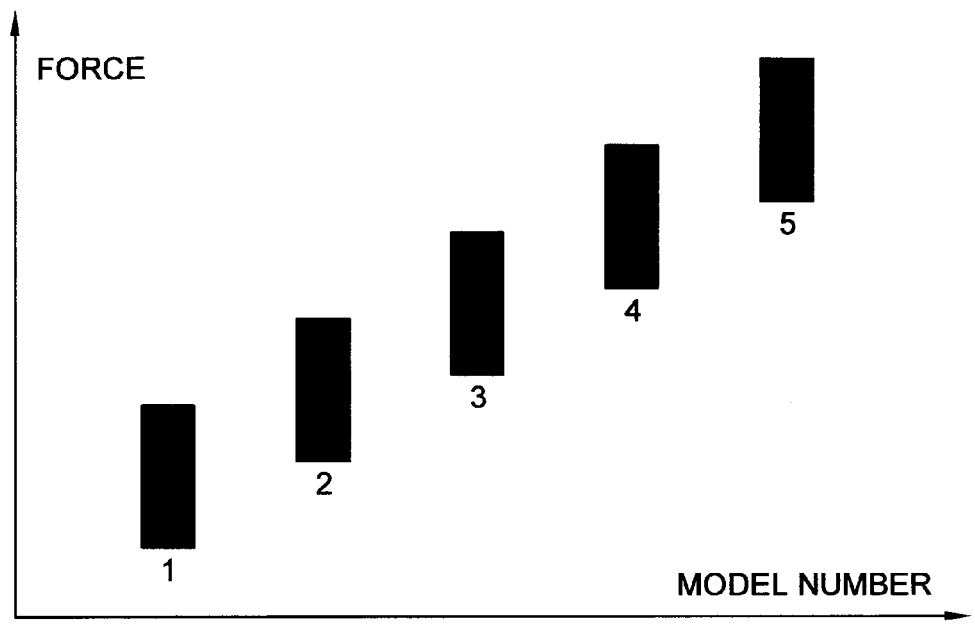
FIG. 21 is a graph depicting the variety of models of force limiting members and/or force indicating members in relation to force.
Figure 22:
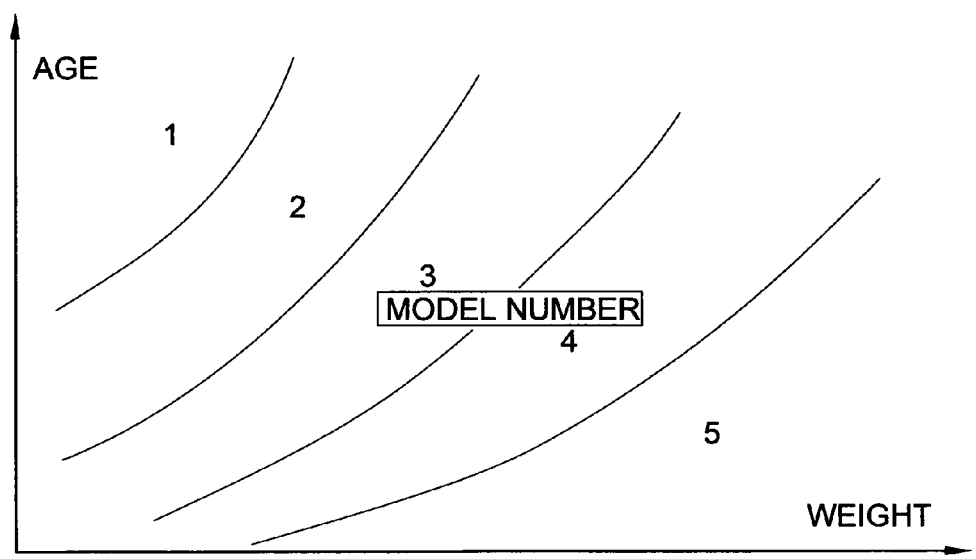
FIG. 22 is a graph depicting the variety of models of force limiting members and/or force indicating members in relation to weight and age of a subject.

Rather than adjust a single device, it is also envisaged that individual devices may be provided having varying force limiting qualities. The graphs in FIGS. 21 and 22 reflect various models of device suitable for certain force ranges and also suitable for different ages and weight (bone quality).

Figure 20A:
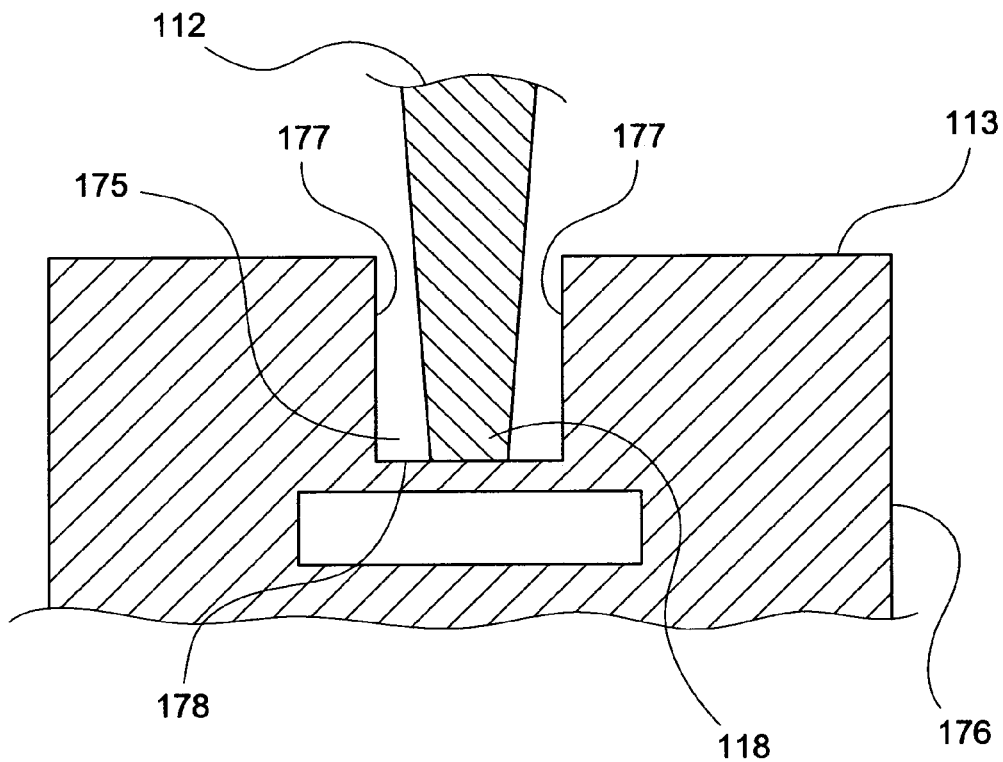
FIGS. 20a and 20b show cross-sectional views of part of an implant having a force limiting means.
Figure 20B:
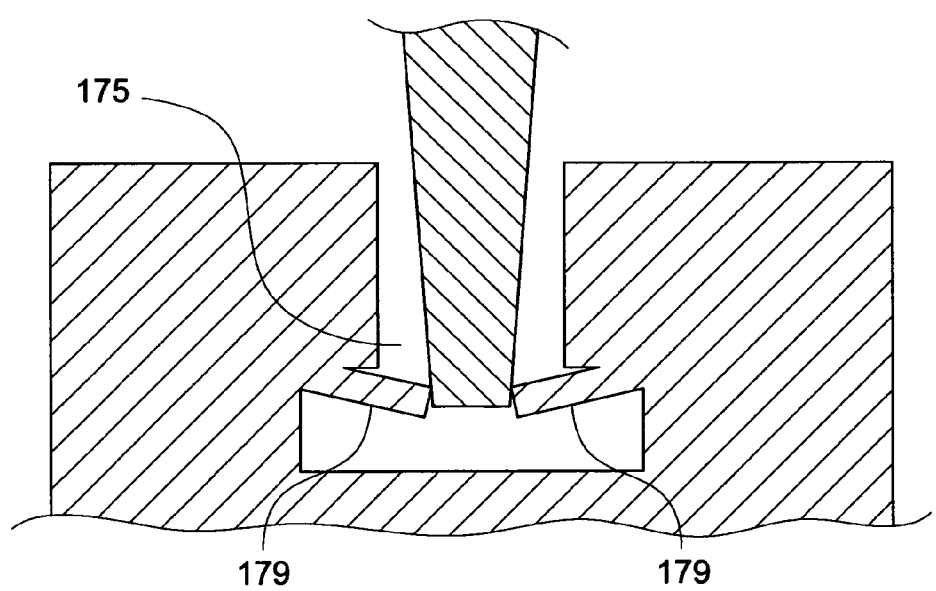

The implant 113 itself may have either or both of a force limiting member and a force indicator member. In the embodiment depicted in FIGS. 20a and 20b, the implant 113 has a recess 175 at a proximal end 176 to receive the second end 118 of the impactor 112. The recessed region is defined by sidewalls 177 and a base 178. The base comprises a plate member 179 which is configured to fail when subjected to a force representative of the load limit of the bone. When the plate member 179 fails the second end 118 of the impactor 112 has no bearing surface and thus the force that may thereafter be applied to the implant is significantly reduced thus reducing the risk of fracture to the subject bone.

In a further aspect of the safety system, a tracking system is used to assess fracture risk. An example illustrating the use of a device and method subject of this aspect is set out below in Example 1.

Example 1

(i) Co-ordinates of several landmarks are used to construct femoral and acetabular reference frames which are then exported as text files.
(ii) Co-ordinates of a tool tracker in the relevant reference frame (femoral or acetabular) are exported with associated time values, e.g
    At t=t1, the tool tracker will be at co-ordinates; (x1, y1, z1).
    Then t=t2 the tool tracker will be at co-ordinates (x2, y2, z2).
(iii) Data processing, the time based positions of the tool tracker are processed relative to the reference frames.
(iv) The relative velocity and relative acceleration of the components can be calculated. With the time based co-ordinates of the tool tracker and the relevant geometry of the component/implant obtained this enables a reconstruction of the relevant geometry of the prosthetic components, or a segment of the component that is of interest, for example the apex of the cup or the distal tip of the stem.
(v) The processed data is further processed comparatively against pre-determined displacement values (eg achieved from cadaveric studies an example of which is provided below). The output is an indicator of the risk of bone fracture based on the degree of displacement of the prosthetic components in light of reference values known to cause fracture.

Each impaction by the surgeon and the relevant displacement caused by the impaction may be filtered from the processed data. This provides a means to determine a diminishing displacement to the extent that said diminished displacement is predictive of fracture.

A surgeon interface which alerts the surgeon of imminent failure is therefore provided. The interface may include a graphical display of a fracture risk threshold as the surgeon progressively seats the component.

Figure 23:
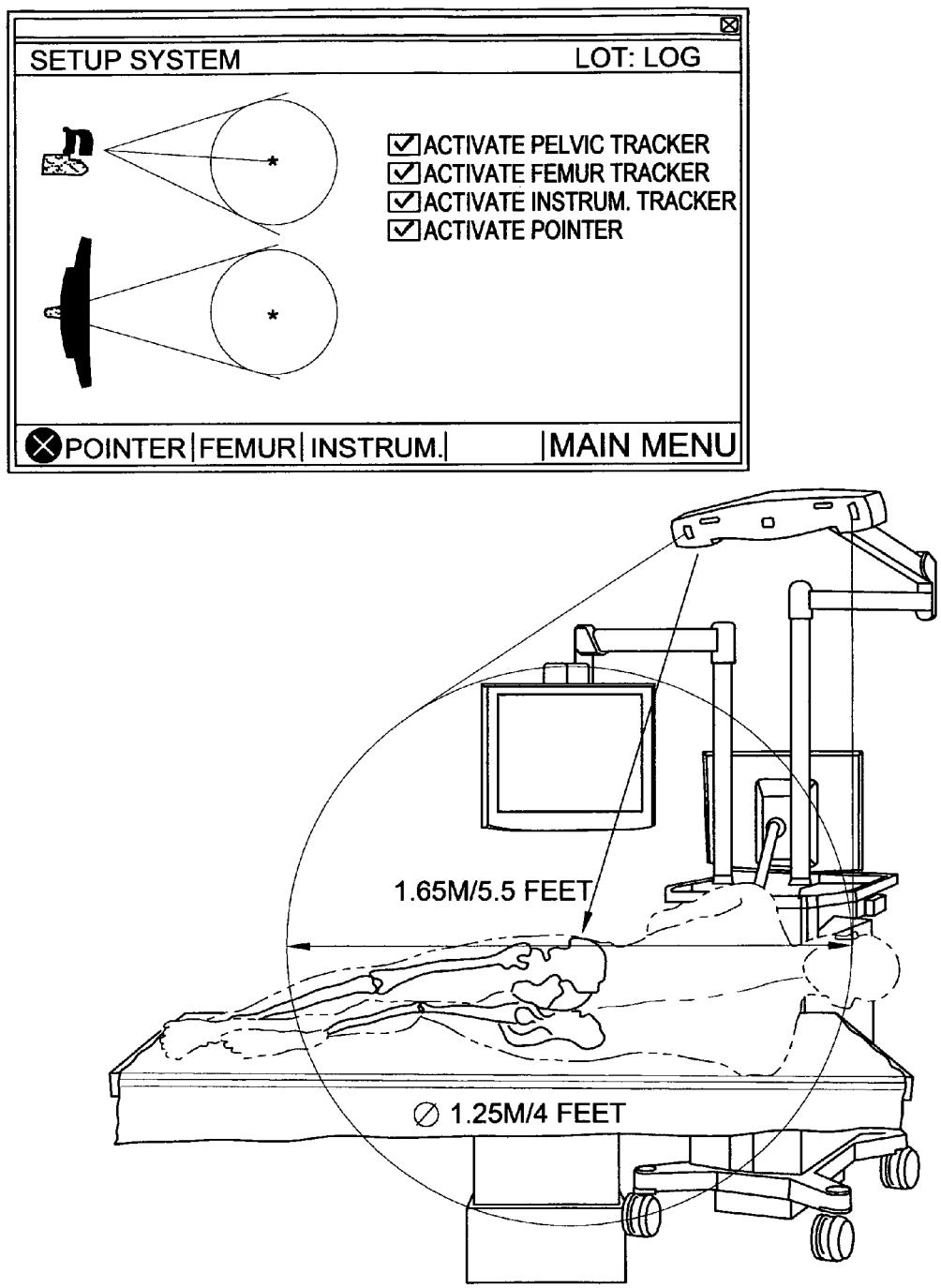
FIG. 23 is a representation of the operating position and system for Navigated Total Hip Surgery.
Figure 24:
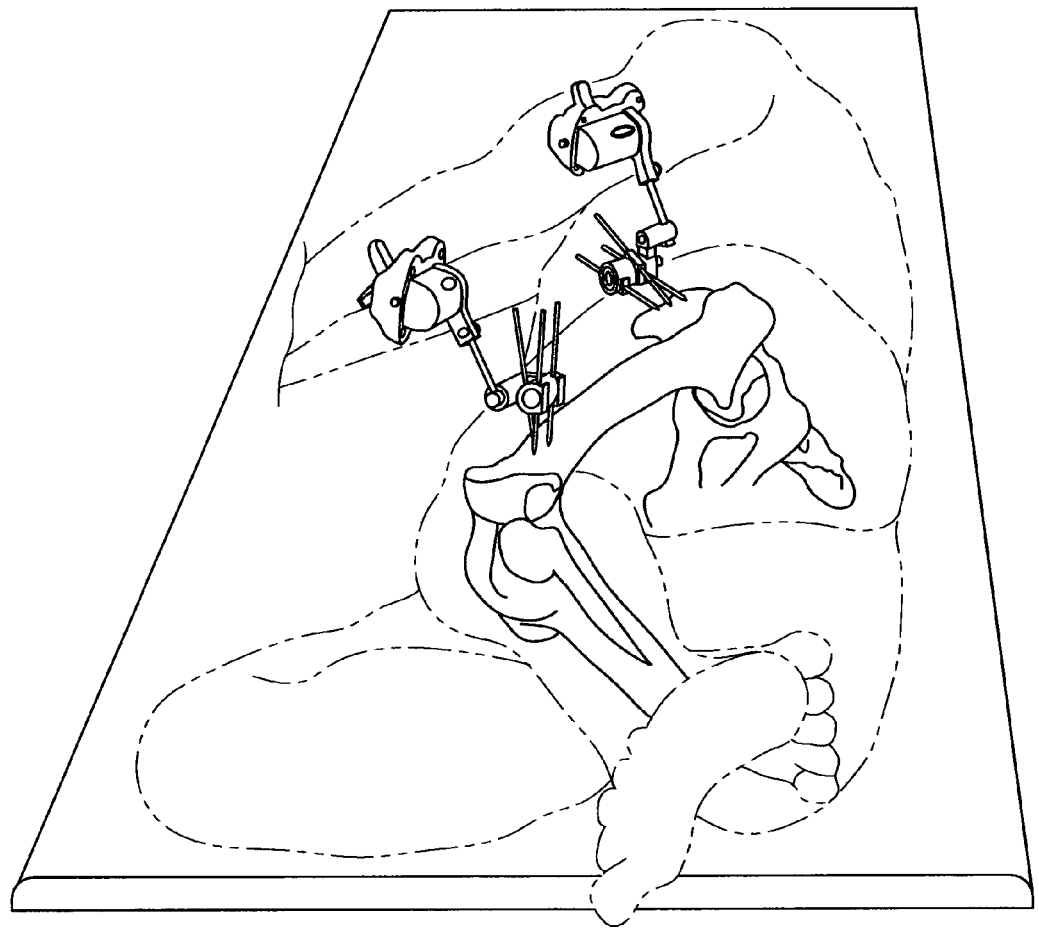
FIG. 24 is a representation of the placement of device trackers relative to the patient.

Cadaveric Studies
Preparation for Patient-Specific Finite Element Models:
(i) Before CT scanning insert cranio-maxillo-facial Titanium bone screws as fiduciary markers in locations that allow simple digitization with Hip navigation pointer;
(ii) CT Scans of pelves and femora performed with a water calibration phantom wherein;
the scans are no overlapping contiguous, slices of the smallest slice thickness achievable.
(iii) Dicom files are provided on a readily readable digital media. (CDR, DVDR or USB stick)
Measurement of the Displacement of Components Relative to Bone During Simulated Intra-Operative Per-Prosthetic Fracture:
(i) A cadaver/saw bone model is positioned to represent the patient in final lateral position on the operating table ready for Navigated Total Hip Surgery as shown in FIG. 23;
(ii) A Navigation Camera is placed opposite but towards the head of the patient;
(iii) Ortholock fixation device trackers placed on ipsolateral side, anterior superior iliac spin (ASIS) and the ipsolateral distal femur as shown in FIG. 24;
(iv) Full Femoral and pelvic Navigation activated to ensure co-ordinates of digitized points and reference frames are recorded;
(v) Fiduciary markers are digitised as research points in pre determined order;
(vi) Instrumented Mallet set up with accelerometer (ensure accelerometer recording software is activated on Navigational System PC).

Figure 25:
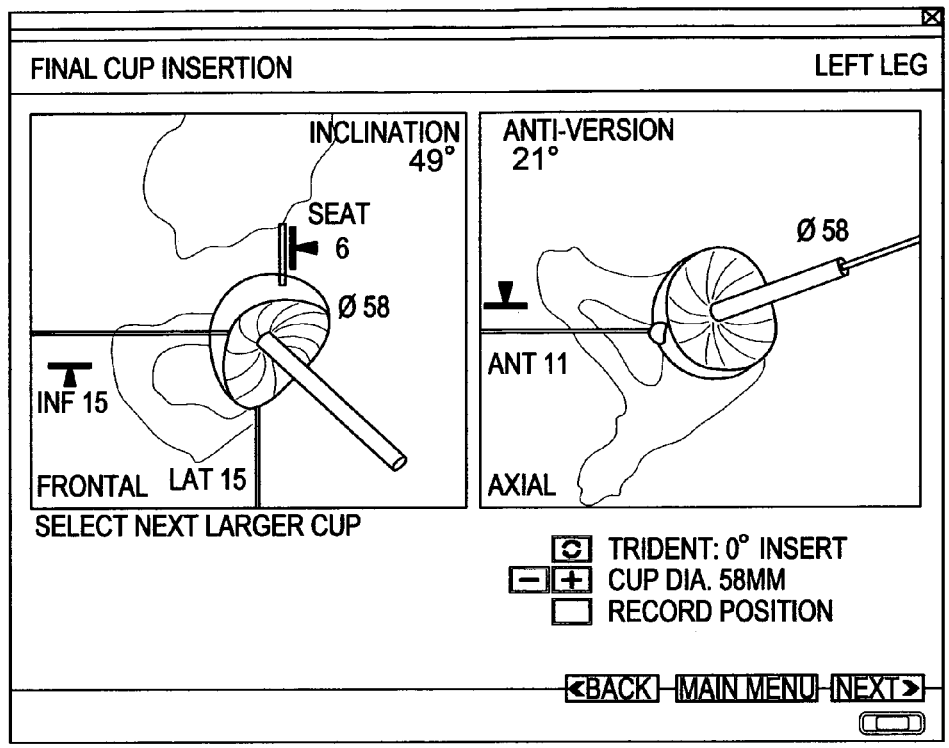
FIG. 25 is a representation of acetabular cup insertion.
Figure 25:
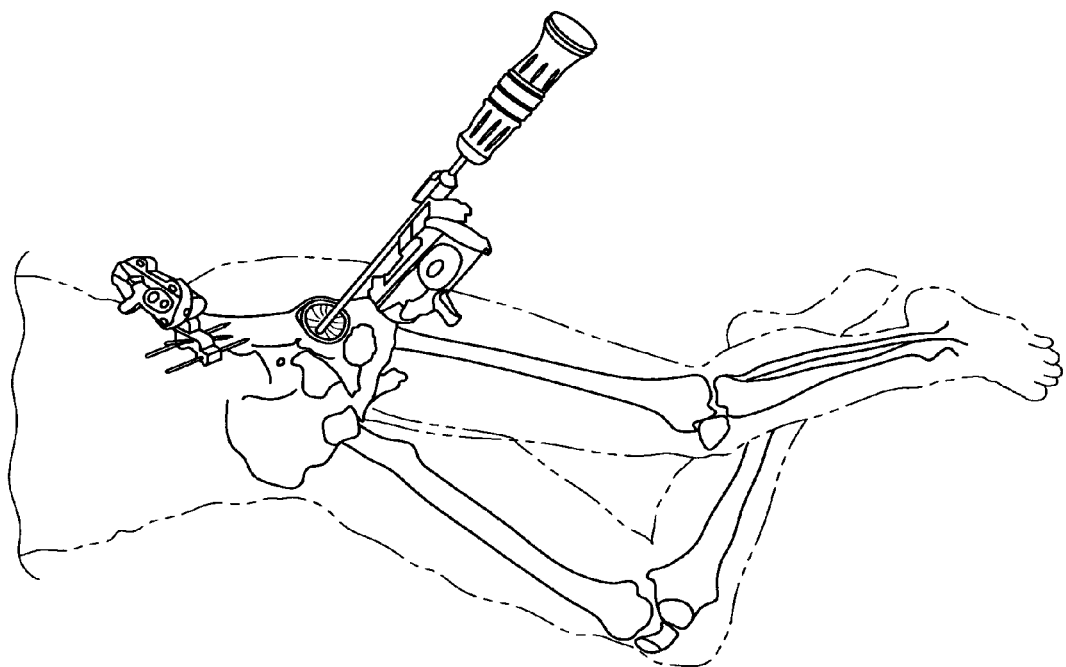

As depicted in FIG. 25, the next stage of the cadaveric studies is to record time dependent co-ordinates of an acetabular cup component of a prosthesis relative to the pelvic reference frame during cup insertion with induced peri-prosthetic fracture, including the following steps:
Acetabular Studies
(i) Ensure pelvis is supported as it would be in surgery (or if using saw bones ensure pelvis is firmly clamped).
(ii) Prepare the acetabulum as per normal surgical technique including:
reaming using the Navigation system as an alignment guide to attempt to keep reaming orientation as close as possible to ideal cup position with reference to anterior pelvic plane (ie 45 inclination 25 anti-version);
trial—ie assess the appropriate cup size using window trials. Navigation should be used as a guide for inclination and version.
(iii) After the appropriate cup size is determined by trialing, purposely oversize the cup component to ensure a peri-prosthetic fracture is induced during cup impaction;
(iv) Use instrumented mallet with accelerometer attached to seat the cup and induce peri prosthetic fracture.

It is important to ensure that the co-ordinates of the instrument tracker (cup position) with reference to the pelvic tracker (pelvic reference frame) are recorded at highest possible frequency during cup insertion and subsequent inducement of fracture.

Figure 26:
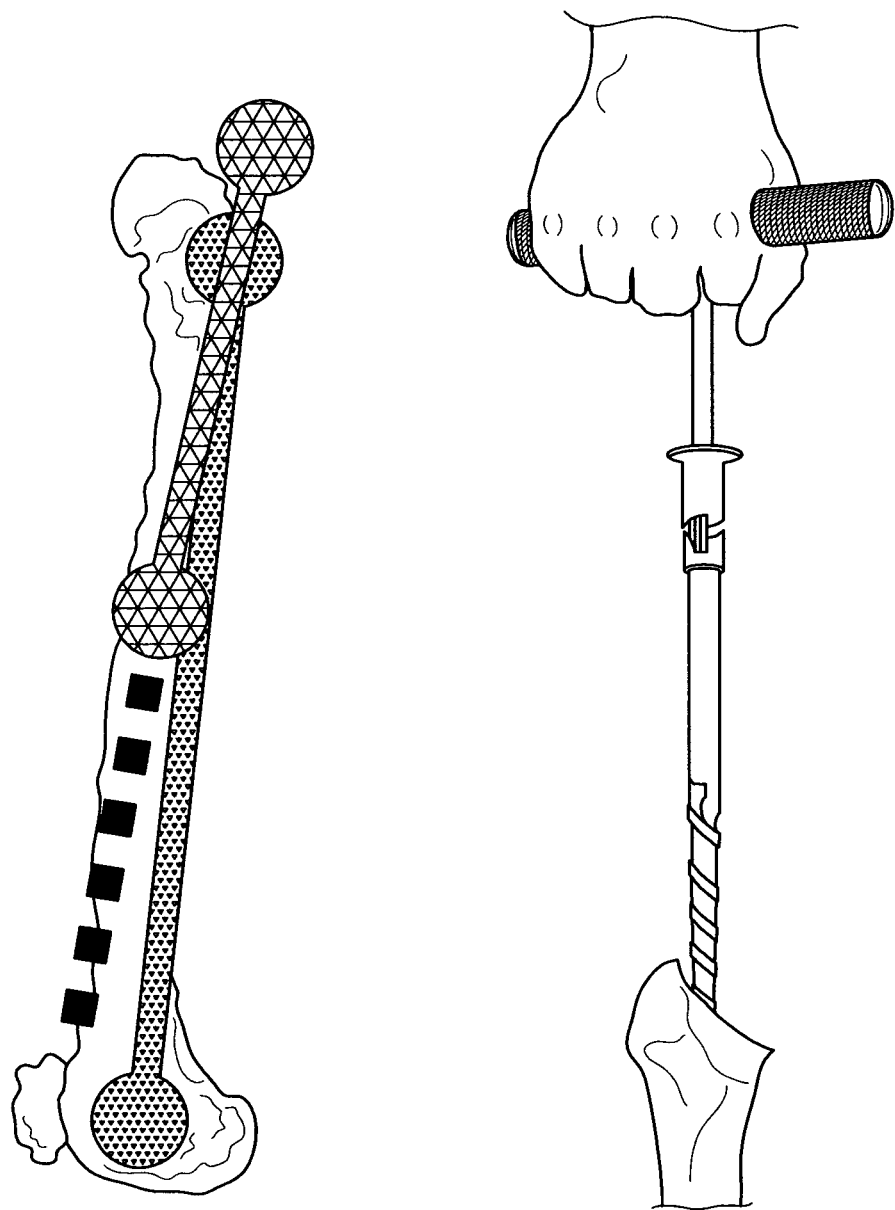
FIG. 26 depicts preparation of the femur.
Figure 27:
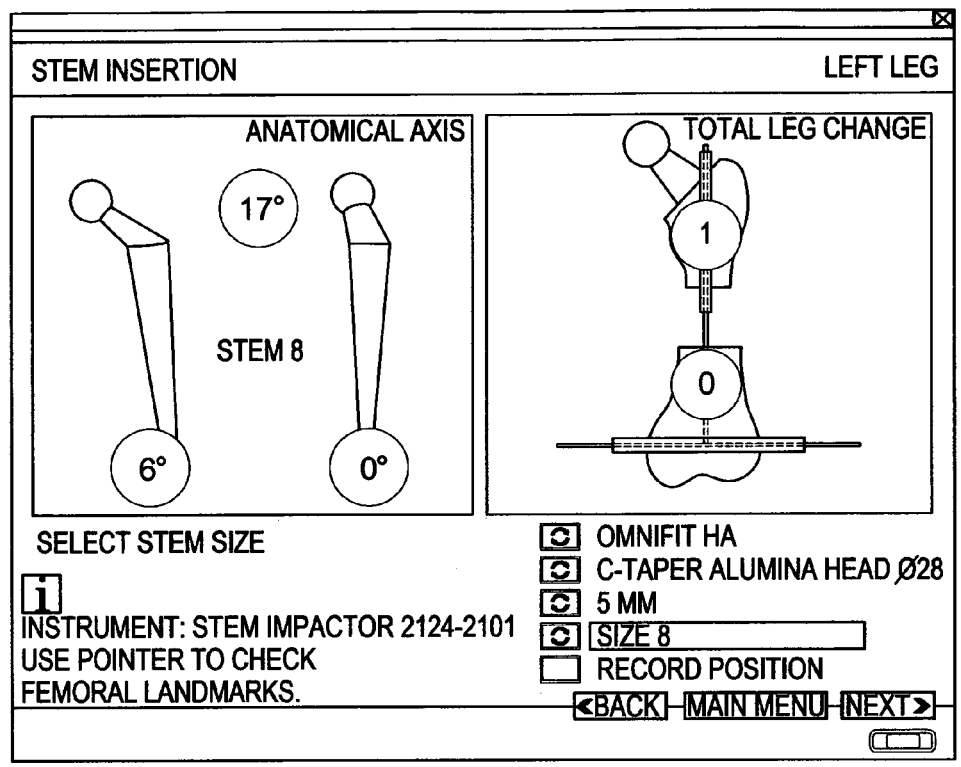
FIG. 27 depicts femoral stem insertion.
Figure 27:
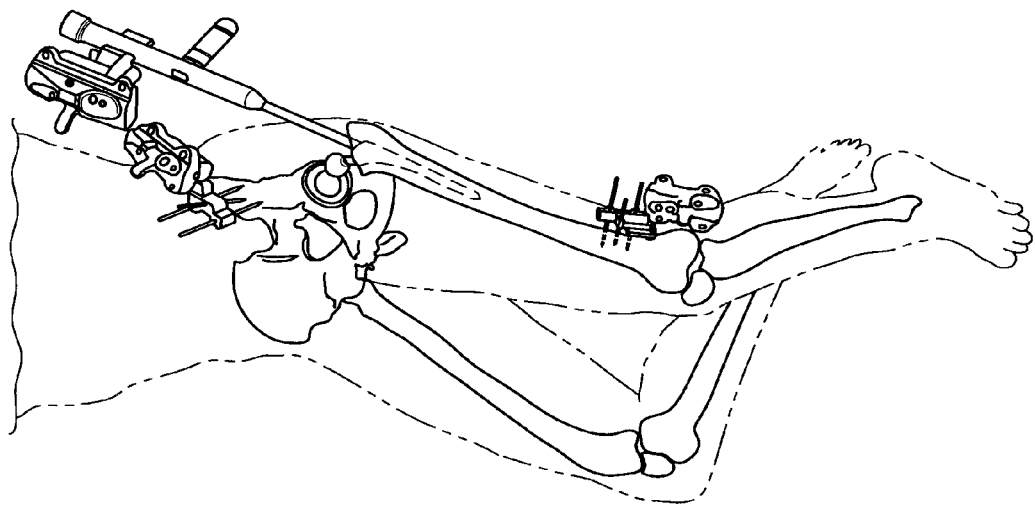

As depicted in FIG. 25, the next stage includes recording time dependent co-ordinates of the femoral component relative to the femoral reference frame during trial/definitive stem insertion with induced peri-prosthetic fracture.
Femoral Studies
(i) Ensure femur is supported by soft tissue as it would be during normal surgery (or if using saw bone ensure distal segment of saw bone is firmly clamped);
(ii) Prepare the femur as per the surgical technique:
ensuring that the straight reamer is used to digitize the anatomical axis of the femur in the femoral reference frame (see FIGS. 26 and 27);
ream the appropriate distal diameter as per ABG II surgical technique;
broach until appropriate femoral component size is determined.
(iii) After the appropriate size is determined, purposely select the next largest broach/definitive stem to ensure a peri-prosthetic fracture is induced during impaction;
(iv) Use instrumented mallet with accelerometer attached to insert the stem and induce peri-prosthetic fracture.

Again, it is important to ensure that the co-ordinates of the instrument tracker (femoral component position) with reference to the femoral tracker (femoral reference frame) are recorded at highest possible frequency during insertion and inducement of fracture.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive:

The invention claimed is:

1. A force indicator member for use with an orthopaedic implant system, wherein the force indicator member comprises a main body having a connection member to connect the main body to a driving member or to an implant of the orthopaedic implant system, and
wherein the main body of the force indicator is configured to receive a force applied to implant an orthopaedic implant into a bone of a subject, the force indicator comprising a frangible structure, the frangible structure configured to break above a pre-determined force applied to the main body and further wherein, the force indicator member generates a signal to a user upon breaking of the frangible structure, the signal indicative of a risk of fracture to the bone.

2. A method of implanting an orthopaedic implant into a bone without fracturing the bone, the method comprising:
exposing an area of subject bone;
preparing the bone for insertion of an implant; and
applying force using a driving member to the implant to drive the implant into the bone,
wherein the implant or the driving member comprise or are connected to a force indicator member, and
wherein the force indicator member comprises
a frangible structure, the frangible structure configured to break above a pre-determined force applied to the main body and further wherein, the force indicator member generates a signal to a user upon breaking of the frangible structure, the signal indicative of a risk of fracture to the bone.

3. The force indicator member of claim 1, wherein the signal is a visual signal.

4. The force indicator member of claim 3, wherein the visual signal includes a light, and wherein illumination of the light is indicative of risk of fracture to the bone.

5. The force indicator member of claim 3, wherein the visual signal includes a plurality of lights, and wherein the greater the number of lights which are illuminated is indicative of a greater risk of fracture to the bone.

6. The force indicator member of claim 1, wherein the signal is an auditory signal.

7. The force indicator member of claim 1, wherein the main body comprises at least one moveable plate which is moveable by application of the force applied to implant the orthopaedic implant.

8. The force indicator member of claim 7, wherein the frangible structure comprises a balloon member, and wherein movement of the moveable plate by or above a pre-determined distance causes rupture of the balloon member.

9. The force indicator member of claim 8, wherein the balloon member contains a marker which is released upon rupture of the balloon.

10. The force indicator member of claim 9, wherein the marker includes a dye.

11. The force indicator member of claim 1, wherein the pre-determined force is 1500N.

12. The force indicator member of claim 1, wherein the pre-determined force is 1700N.

13. The force indicator member of claim 1, wherein the signal is generated when the force used to implant the orthopaedic implant is between 1500N and 2000N.

* * * * *